US010858392B2

(12) United States Patent
Yoshida et al.

(10) Patent No.: US 10,858,392 B2
(45) Date of Patent: Dec. 8, 2020

(54) AFFINITY SEPARATION MATRIX FOR PURIFYING PROTEIN CONTAINING IMMUNOGLOBULIN K CHAIN VARIABLE REGION

(71) Applicant: Kaneka Corporation, Osaka (JP)

(72) Inventors: Shinichi Yoshida, Hyogo (JP); Dai Murata, Hyogo (JP)

(73) Assignee: KANEKA CORPORATION, Osaka (JP)

( * ) Notice: Subject to any disclaimer, the term of this patent is extended or adjusted under 35 U.S.C. 154(b) by 193 days.

(21) Appl. No.: 15/660,373

(22) Filed: Jul. 26, 2017

(65) Prior Publication Data

US 2017/0327535 A1    Nov. 16, 2017

Related U.S. Application Data

(63) Continuation of application No. PCT/JP2016/052036, filed on Jan. 25, 2016.

(30) Foreign Application Priority Data

Jan. 26, 2015 (JP) ................................. 2015-012663

(51) Int. Cl.
| | |
|---|---|
| C07K 1/22 | (2006.01) |
| C07K 14/315 | (2006.01) |
| C07K 16/00 | (2006.01) |
| C07K 17/00 | (2006.01) |
| C07K 16/10 | (2006.01) |

(52) U.S. Cl.
CPC .............. *C07K 1/22* (2013.01); *C07K 14/315* (2013.01); *C07K 16/00* (2013.01); *C07K 16/1027* (2013.01); *C07K 17/00* (2013.01); *C07K 2317/55* (2013.01)

(58) Field of Classification Search
None
See application file for complete search history.

(56) References Cited

U.S. PATENT DOCUMENTS

| | | | |
|---|---|---|---|
| 5,143,844 A | 9/1992 | Abrahmsen et al. | |
| 5,965,390 A | 10/1999 | Bjorck et al. | |
| 6,162,903 A | 12/2000 | Trowern et al. | |
| 6,399,750 B1 | 6/2002 | Johansson | |
| 6,831,161 B1 | 12/2004 | Uhlen et al. | |
| 2002/0137918 A1 | 9/2002 | Gore et al. | |
| 2003/0027283 A1 | 2/2003 | Bjorck et al. | |
| 2003/0153735 A1 | 8/2003 | Breece et al. | |
| 2005/0100970 A1 | 5/2005 | Uhlen et al. | |
| 2005/0143566 A1 | 6/2005 | Hober | |
| 2005/0215769 A1 | 9/2005 | Breece et al. | |
| 2006/0134805 A1 | 6/2006 | Berg et al. | |
| 2006/0142549 A1 | 6/2006 | Takeda et al. | |
| 2006/0194950 A1 | 8/2006 | Hober et al. | |
| 2006/0194955 A1 | 8/2006 | Hober et al. | |
| 2007/0178541 A1* | 8/2007 | Pedersen | G01N 33/564 |
| | | | 435/7.32 |
| 2007/0275873 A1 | 11/2007 | Heidner et al. | |
| 2010/0022760 A1 | 1/2010 | Hober et al. | |
| 2010/0286373 A1 | 11/2010 | Majima et al. | |
| 2011/0112276 A1 | 5/2011 | Hober | |
| 2011/0144311 A1 | 6/2011 | Chmielowski et al. | |
| 2012/0238724 A1 | 9/2012 | Hober | |
| 2013/0096276 A1 | 4/2013 | Yoshida et al. | |
| 2013/0184438 A1 | 7/2013 | Hober et al. | |
| 2013/0225796 A1 | 8/2013 | Takeda et al. | |
| 2014/0018525 A1 | 1/2014 | Goklen et al. | |
| 2014/0323695 A1 | 10/2014 | Takeda et al. | |
| 2016/0024146 A1 | 1/2016 | Goklen et al. | |
| 2016/0152668 A1 | 6/2016 | Hober | |
| 2016/0237113 A1 | 8/2016 | Minakuchi | |
| 2017/0159099 A1 | 6/2017 | Beam et al. | |
| 2017/0174721 A1 | 6/2017 | Goklen et al. | |
| 2017/0320919 A1* | 11/2017 | Rodrigo | C07K 14/195 |
| 2017/0334947 A1 | 11/2017 | Murata et al. | |
| 2018/0036445 A1 | 2/2018 | Monie et al. | |
| 2019/0144511 A1 | 5/2019 | Rodrigo et al. | |

FOREIGN PATENT DOCUMENTS

| | | | |
|---|---|---|---|
| CN | 1634990 A | * | 7/2005 |
| CN | 1634990 A | | 7/2005 |
| EP | 1123389 A1 | | 8/2001 |
| EP | 3153581 A1 | | 4/2017 |
| JP | H07506573 A | | 7/1995 |
| JP | H07507682 A | | 8/1995 |
| JP | 2006304633 A | | 11/2006 |
| JP | 2007252368 A | | 10/2007 |

(Continued)

OTHER PUBLICATIONS

International Search Report issued in International Application No. PCT/JP2016/052036; dated Apr. 19, 2016 (2 pages).
International Search Report issued in International Application No. PCT/JP2017/015500; dated Jul. 18, 2017 (2 pages).
International Search Report issued in International Application No. PCT/JP2016/052038; dated Apr. 12, 2016 (2 pages).
Hober et al., "Protein A chromatography for antibody purification", Journal of Chromatography B, 848 (2007) pp. 40-47 (8 pages).
Shukla et al., "Recent advances in large-scale production of monoclonal antibodies and related proteins", Trends in Biotechnology, vol. 28, No. 5, pp. 253-261 (9 pages).
Nelson et al., "Development trends for therapeutic antibody fragments", Nature Biotechnology, vol. 7, No. 4, Apr. 2009, pp. 331-337 (7 pages).

(Continued)

*Primary Examiner* — Daniel E Kolker
*Assistant Examiner* — James L Rogers
(74) *Attorney, Agent, or Firm* — Osha Bergman Watanabe & Burton LLP

(57) ABSTRACT

An affinity separation matrix includes a water-insoluble base material; and a ligand that is immobilized on the water-insoluble base material, wherein the ligand is an antibody κ chain variable region-binding peptide comprising B5 domain of Protein L derived from *Peptostreptococcus magnus* 312 strain or a part thereof.

5 Claims, 4 Drawing Sheets
Specification includes a Sequence Listing.

(56) References Cited

FOREIGN PATENT DOCUMENTS

| | | |
|---|---|---|
| JP | 2008523140 A | 7/2008 |
| JP | 2009/196998 A | 9/2009 |
| JP | 2011/006489 A | 1/2011 |
| JP | 2011-530606 A | 12/2011 |
| JP | 2016079149 A | 5/2016 |
| WO | 199717361 A1 | 5/1997 |
| WO | 0015803 A1 | 3/2000 |
| WO | 03080655 A1 | 10/2003 |
| WO | 2005/033130 A2 | 4/2005 |
| WO | 2005113584 A1 | 12/2005 |
| WO | WO-2005113584 A1 * 12/2005 | ......... A61K 39/0208 |
| WO | 2006126942 A1 | 11/2006 |
| WO | WO-2007019376 A2 * 2/2007 | ........... A61K 49/085 |
| WO | 2011118699 A1 | 9/2011 |
| WO | 2012/135415 A1 | 10/2012 |
| WO | 2014/141150 A1 | 9/2014 |
| WO | 2015041218 A1 | 3/2015 |
| WO | 2015190457 A1 | 12/2015 |
| WO | 2015190458 A1 | 12/2015 |
| WO | 2016031902 A1 | 3/2016 |
| WO | 2016121701 A1 | 8/2016 |

OTHER PUBLICATIONS

Bouvet, "Immunoglobulin Fab Fragment-Binding Proteins", Int. J. Immunopharmac., vol. 16, No. 5/6, 1994, pp. 419-424 (6 pages).
Kastern et al., "Structure of Peptostreptococcal Protein L and Identification of a Repeated Immunoglobulin Light Chain-binding Domain", The Journal of Biological Chemistry, vol. 267, No. 18, Jun. 25, 1992, pp. 12820-12825 (6 pages).
Murphy et al., "The functional units of a peptostreptococcal preotein L", Molecular Microbiology, 1994, vol. 12, No. 6, pp. 911-920 (10 pages).
Housden et al., "Immunoglobulin-binding domains: Protein L from Peptostreptococcus magnus", Biochemical Society Transactions, 2003, vol. 31, Pt. 3, pp. 716-718 (3 pages).
Kihlberg et al., "Protein LG: A Hybrid Molecule with Unique Immunoglobulin Binding Properties", The Journal of Biological Chemistry, vol. 267, No. 35, Dec. 15, 1992, pp. 25583-25588 (6 pages).
Svensson et al., "Protein LE, a novel hybrid protein with unique single-chain Fv antibody- and Fab-binding properties", European Journal of Biochemistry, vol. 258, 1998, pp. 890-896 (7 pages).
Graille et al., "Complex between Peptostreptococcus magnus Protein L and a Human Antibody Reveals Structural Convergence in the Interaction Modes of Fab Binding Proteins", Structure, vol. 9, Aug. 2001, pp. 679-687 (9 pages).
Bottomley et al., "Cloning, expression and purification of Ppl-1, a kappa-chain binding protein, based upon protein L from Peptostreptococcus magnus", Bioseparation, vol. 5, 1995, pp. 359-367 (9 pages).
Capto (TM) L, Aug. 2014, [online] [retrieval date Apr. 11, 2016] <https://www.gelifescience.com/gehcls_images/GELS/Related%20Content/Files/1346418936586/litdoc29010008_20141004004020.pdf> (8 pages).
Housden et al., "Observation and Characterization of the Interaction between a Single Immunoglobulin Binding Domain of Protein L and Two Equivalents of Human k Light Chains", The Journal of Biological Chemistry, vol. 279, No. 10, Mar. 5, 2004, pp. 9370-9378 (9 pages).
Tadeo et al, "Protein Stabilization and the Hofmeister Effect: The Role of Hydrophobic Solvation", Biophysical Journal, vol. 97, Nov. 2009, pp. 2595-2603 (9 pages).
Glyakina et al., "Mechanical stability analysis of the protein L immunoglobulin-binding domain by full alanine screening using molecular dynamics simulations", Biotechnology Journal, 2015, vol. 10, pp. 386-394 (11 pages).

Svensson et al., "Contributions of Amino Acid Side Chains to the Kinetics and Thermodynamics of the Bivalent Binding of Protein L to Ig k Light Chain", Biochemistry, 2004, vol. 43, pp. 2445-2457 (13 pages).
Millet et al., "The Effects of Mutations on Motions of Side-chains in Protein L Studied by 2H NMR Dynamics and Scalar Couplings", J. Mol. Bio., 2003, vol. 329, pp. 551-563 (13 pages).
Beckingham et al., "Interactions between a single immunoglobulin-binding domain of protein L from Petpostreptococcus magnus and a human k light chain", Biochem. J., 1999, vol. 340, pp. 193-199 (7 pages).
Yoshida et al., "Rational design and engineering of protein A to obtain the controlled elution profile in monoclonal antibody purification", Chem-Bio Informatics Journal, vol. 12, 2012, pp. 1-13 (13 pages).
Palmgren et al., "Improving the alkali stability of the k light chain-binding polypetide from domain of peptostreptoccu protein L", Abstracts of Papers, 251st ACS National Meeting & Exposition, Mar. 3, 2016 (Abstract) (1 page).
D. E. Kim et al. "A Breakdown of Symmetry in the Folding Transition State of Protein L", Journal of Molecular Biology, 2000, vol. 298, No. 5, pp. 971-984 (14 pages).
X Yang et al. "Total chemical synthesis of the B1 domain of protein L from Peptostreptococcus magnus", Bioorganic Chemistry 2006, vol. 34, No. 3, pp. 131-141 (11 pages).
Extended European Search Report issued in European Application No. 16743306.9, dated Jun. 15, 2018 (8 pages).
Nelson et al., "Development trends for therapeutic antibody fragments", Nature Biotechnology, vol. 27, No. 4, Apr. 2009, pp. 331-337 (7 pages).
Svensson et al., "Protein LA, a novel hybrid protein with unique single-chain Fv antibody- and Fab-binding properties", European Journal of Biochemistry, vol. 258, 1998, pp. 890-896 (7 pages).
Palmgren et al., "Improving the alkali stability of the kappa light chain-binding polypeptide from domain of peptostreptococcus protein L", Abstracts of Papers, 251st ACS National Meeting & Exposition, Mar. 3, 2016 (Abstract) (1 page).
Beckingham et al., "Interactions between a single immunoglobulin-binding domain of protein L from peptostreptococcus magnus and a human k light chain", Biochem. J., 1999, vol. 340, pp. 193-199 (7 pages).
Murphy et al., "The functional units of a peptostreptococcal protein L", Molecular Microbiology, 1994, vol. 12, No. 6, pp. 911-920 (10 pages).
Capto (TM) L, Aug. 2014, [online] [retrieval date Apr. 11, 2016] <https://www.gelifesciences.com/gehcls_images/GELS/Related%20Content/Files/1346418936586/litdoc29010008_20141004004020.pdf> (8 pages).
Millet et al., "The Effects of Mutations on Motions of Side-chains in Protein L Studied by 2H NMR Dynamics and Scalar Couplings", J. Mol. Biol., 2003, vol. 329, pp. 551-563 (13 pages).
M. Kastner, "Protein liquid chromatography," Journal of Chromatography Library, vol. 61, section 22.5.2, p. 811, 2000 (3 pages).
Office Action issued in U.S. Appl. No. 16/176,090; dated Oct. 1, 2019 (27 pages).
GE Healthcare Bio-Science AB, "Capto TM L"; Affinity chromatography; gelifesciences.com, Data file 29-0100-08 AC; (8 pages).
A. Murray et al, "Epitope Affinity Chromatography and Biophysical Studies of Monoclonal Antibodies and Recombinant Antibody Fragments", Journal of Chromatographic Science; vol. 40, Jul. 2002; pp. 343-349 (7 pages).
B. R. Hubbard et al, "Vitamin K-dependent carboxylase: Affinity purification from bovine liver by using a synthetic propeptide containing the Y-carboxylation recognition site", Proceedings of the National Academy of Sciences of the United States of America; vol. 86, Sep. 1989; pp. 6893-6897 (6 pages).

* cited by examiner

AFFINITY SEPARATION MATRIX FOR PURIFYING PROTEIN CONTAINING IMMUNOGLOBULIN K CHAIN VARIABLE REGION

TECHNICAL FIELD

One or more embodiments of the present invention relate to an affinity separation matrix having an immunoglobulin κ chain variable region-containing protein-binding peptide of which binding capability to an immunoglobulin κ chain variable region is excellent as a ligand, a method for producing an immunoglobulin κ chain variable region-containing peptide by using the affinity separation matrix, a DNA encoding the peptide, a vector containing the DNA, and a transformant transformed by the vector.

BACKGROUND

As one of important functions of a protein, a capability to specifically bind to a specific molecule is exemplified. The function plays an important role in an immunoreaction and signal transduction in a living body. A technology utilizing the function for purifying a useful substance has been actively developed. As one example of proteins which are actually utilized industrially, for example, Protein A affinity separation matrix has been used for capturing an antibody drug to be purified with high purity at one time from a culture of an animal cell (Non-patent documents 1 and 2). Hereinafter, Protein A is abbreviated as "SpA" in some cases.

An antibody drug which has been developed is mainly a monoclonal antibody, and a monoclonal antibody has been produced on a large scale by using recombinant cell cultivation technology. A "monoclonal antibody" means an antibody obtained from a clone derived from a single antibody-producing cell. Most of antibody drugs launched presently are classified into an immunoglobulin G (IgG) in terms of a molecular structure. In addition, an antibody drug consisting of an antibody fragment has been actively subjected to clinical development. An antibody fragment is an antibody derivative having a molecular structure obtained by fragmenting IgG. A plurality of antibody drugs consisting of such an antibody fragment have been clinically developed (Non-patent Document 3).

In an initial purification step in an antibody drug production, the above-described SpA affinity separation matrix is utilized. However, SpA is basically a protein which specifically binds to a Fc region of IgG. Thus, SpA affinity separation matrix cannot capture an antibody fragment which does not contain a Fc region. Accordingly, an affinity separation matrix capable of capturing an antibody fragment which does not contain a Fc region of IgG is highly required industrially in terms of a platform development of a process for purifying an antibody fragment.

A plurality of peptides which can bind to a region except for a Fc region of IgG have been already known (Non-patent Document 4). Among such peptides, a peptide which can bind to a variable region, i.e. an antigen-binding domain, is the most preferred in terms of many kinds of an antibody fragment format to be bound and a capability to bind to IgM and IgA, and for example, Protein L is well-known as the peptide. Hereinafter, Protein L is abbreviated to "PpL". PpL is a protein which contains a plurality of κ chain variable region-binding domains. Hereinafter, a κ chain variable region is abbreviated as "VL-κ". In PpL, the amino acid sequences of each VL-κ-binding domain are different. The number of VL-κ-binding domains and the amino acid sequence of each VL-κ-binding domain are different depending on the kind of a strain. For example, the number of VL-κ-binding domains in PpL of *Peptostreptococcus magnus* 312 strain is five, and the number of VL-κ-binding domains in PpL of *Peptostreptococcus magnus* 3316 strain is four (Non-patent Documents 5 to 7, Patent Documents 1 and 2). The amino acid sequences of the above nine VL-κ-binding domains are different from each other.

A plurality of affinity separation matrices having PpL as a ligand have been commercially available. In the case of SpA, it has been actively researched that a recombinant peptide prepared by linking a plurality of specific one kind of antibody-binding domains is used as a ligand (Non-patent Document 1). On the one hand, in the case of PpL, the difference of physical properties and functions of each VL-κ-binding domain due to the difference of the amino acid sequences has been hardly studied, and there is still room for improvement.

Patent Document 1: JP H7-506573 T
Patent Document 2: JP H7-507682 T
Non-patent Document 1: Hober S., et al., J. Chromatogr. B, 2007, vol. 848, pp. 40-47
Non-patent Document 2: Shukla A. A., et al., Trends Biotechnol., 2010, vol. 28, pp. 253-261
Non-patent Document 3: Nelson A. N., et al., Nat. Biotechnol., 2009, vol. 27, pp. 331-337
Non-patent Document 4: Bouvet P. J., Int. J. Immunopharmac., 1994, vol. 16, pp. 419-424
Non-patent Document 5: Kastern W., et al., J. Biol. Chem., 1992, vol. 267, pp. 12820-12825
Non-patent Document 6: Murphy J. P., et al., Mol. Microbiol., 1994, vol. 12, pp. 911-920
Non-patent Document 7: Housden N. G., et al., Biochemical Society Transactions, 2003, vol. 31, pp. 716-718

Under the above-described circumstance, one or more embodiments of the present invention provide an affinity separation matrix which has strong affinity for an immunoglobulin κ chain variable region and which is useful for purifying an immunoglobulin κ chain variable region-containing protein. Also, one or more embodiments of the present invention provide a method for producing an immunoglobulin κ chain variable region-containing peptide by using the affinity separation matrix, a DNA encoding the peptide, a vector containing the DNA, and a transformant transformed by the vector.

The inventors found that when an affinity separation matrix having Protein L (PpL) as a ligand is preliminarily evaluated, there is a large difference between chromatography profiles depending on the kind of an antibody fragment although the light chain is κ chain. Specifically, depending on the kind and sequence of an antibody fragment, a coupling capacitance may be small, a leakage may be observed during an intermediate washing, and stronger acid may be necessary for elution by an acid. Accordingly, the inventors compared the properties of 9 kinds of VL-κ-binding domains of PpL derived from *Peptostreptococcus magnus* 312 strain and 3316 strain as an affinity ligand, and developed a method in which B5 domain of PpL derived from 312 strain or apart thereof is used as a ligand.

SUMMARY

Hereinafter, one or more embodiments of the present invention is described.
[1] An affinity separation matrix,
comprising a water-insoluble base material and a ligand,
wherein the ligand is immobilized on the water-insoluble base material, and the ligand is an antibody κ chain variable region-binding peptide comprising B5 domain of Protein L derived from *Peptostreptococcus magnus* 312 strain or a part thereof.

[2] The affinity separation matrix according to the above [1], wherein an amino acid sequence of the antibody κ chain variable region-binding peptide is any one of the following amino acid sequences:

(1) an amino acid sequence of SEQ ID NO: 7 or SEQ ID NO: 16;

(2) an amino acid sequence of SEQ ID NO: 7 or SEQ ID NO: 16 with deletion, substitution and/or addition of 1 or more and 10 or less amino acid residues, having a binding capability to an antibody κ chain variable region;

(3) an amino acid sequence with a sequence identity of 85% or more to the amino acid sequence of SEQ ID NO: 7 or SEQ ID NO: 16, having a binding capability to an antibody κ chain variable region.

[3] The affinity separation matrix according to the above [2], wherein the amino acid sequence of the antibody κ chain variable region-binding peptide corresponds to the amino acid sequence of SEQ ID NO: 7 wherein the $17^{th}$ position is glutamic acid, the $19^{th}$ position is isoleucine, the $20^{th}$ position is tyrosine, the $22^{nd}$ position is glutamic acid, the $25^{th}$ position is threonine, the $26^{th}$ position is valine, the $30^{th}$ position is threonine, the $50^{th}$ position is serine and the $53^{rd}$ position is histidine.

[4] The affinity separation matrix according to the above [2], wherein the amino acid sequence of the antibody κ chain variable region-binding peptide corresponds to the amino acid sequence of SEQ ID NO: 16 wherein the $7^{th}$ position is glutamic acid, the $9^{th}$ position is isoleucine, the $10^{th}$ position is tyrosine, the $12^{th}$ position is glutamic acid, the $15^{th}$ position is threonine, the $16^{th}$ position is valine, the $20^{th}$ position is threonine, the $40^{th}$ position is serine and the $43^{rd}$ position is histidine.

[5] The affinity separation matrix according to any one of the above [2] to [4], wherein the amino acid sequence of the antibody κ chain variable region-binding peptide corresponds to a repetition of the amino acid sequence.

[6] A method for producing a protein comprising an antibody κ chain variable region, comprising the steps of:
contacting the affinity separation matrix according to any one of the above [1] to [5] with a liquid sample comprising the protein comprising the antibody κ chain variable region; and
separating the protein bound to the affinity separation matrix from the affinity separation matrix.

[7] A DNA, encoding the antibody κ chain variable region-binding peptide according to any one of the above [1] to [5].

[8] A vector, comprising the DNA according to the above [7].

[9] A transformant, transformed by the vector according to the above [8].

By using the affinity separation matrix according to one or more embodiments of the present invention, larger kinds of an antibody fragment can be purified. As a result, the affinity separation matrix enable easier platform development for building an industrial purification process. In particular, it is surprised that the affinity separation matrix prepared by immobilizing B5 domain or a part thereof has the above-described properties, since the construct having B1 to B4 domains is mainly evaluated in Patent Document 1 and Non-patent document 4.

DETAILED DESCRIPTION OF THE EMBODIMENTS

Figure 1:
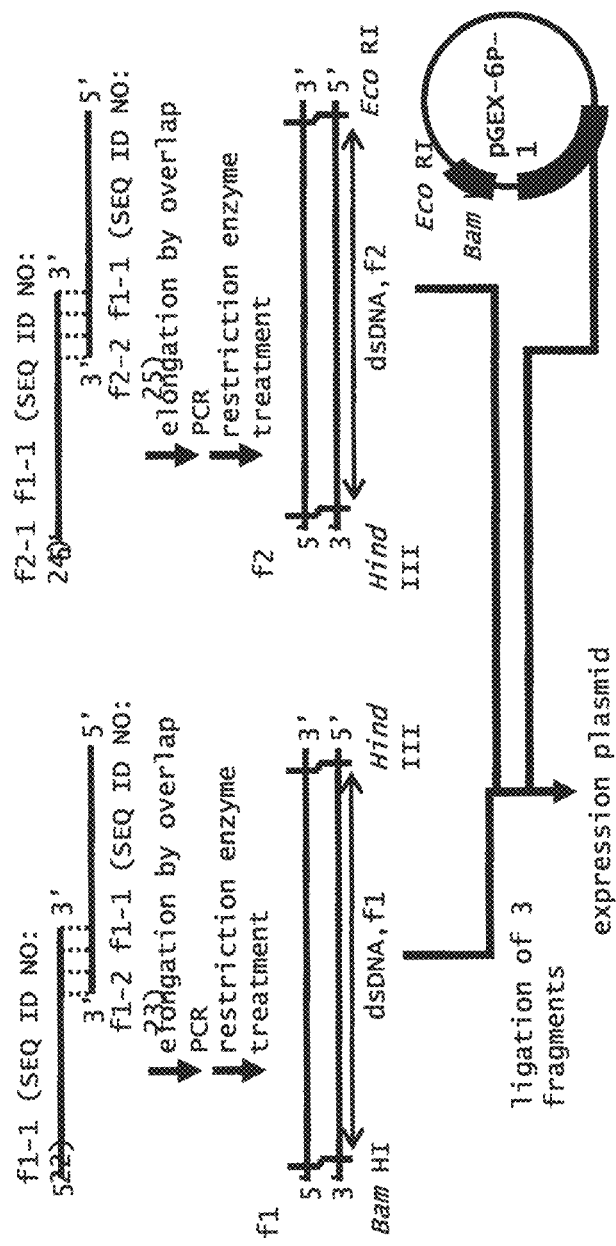
FIG. 1 represents a method for preparing an expression plasmid of LB5t-Wild.1d.

The affinity separation matrix according to one or more embodiments of the present invention is characterized in comprising a water-insoluble base material and a ligand, wherein the ligand is immobilized on the water-insoluble base material, and the ligand is an immunoglobulin κ chain variable region-binding peptide comprising B5 domain of Protein L derived from *Peptostreptococcus magnus* 312 strain or a part thereof. The affinity separation matrix according to one or more embodiments of the present invention have an affinity for various immunoglobulin κ chain variable regions, and for example, is useful for purifying an antibody fragment.

An "immunoglobulin (IgG)" is a glycoprotein produced by a B cell of a lymphocyte and has a function to recognize a molecule such as a specific protein to be bound. An immunoglobulin has not only a function to specifically bind to a specific molecule, i.e. antigen, but also a function to detoxify and remove an antigen-containing factor in cooperation with other biological molecule or cell. An immunoglobulin is generally referred to as "antibody", and the name is inspired by such functions. All of immunoglobulins basically have the same molecular structure. The basic structure of an immunoglobulin is a Y-shaped four-chain structure consisting of two light chains and two heavy chains of polypeptide chains. A light chain (L chain) is classified into two types of λ chain and κ chain, and all of immunoglobulins have either of the chains. A heavy chain (H chain) is classified into five types of γ chain, μ chain, α chain, δ chain and ε chain, and an immunoglobulin is classified into isotypes depending on the kind of a heavy chain. An immunoglobulin G (IgG) is a monomer immunoglobulin composed of two heavy chains (γ chains) and two light chains, and has two antigen-binding sites.

A lower half vertical part in the "Y" shape of an immunoglobulin is referred to as a "Fc region", and an upper half "V" shaped part is referred to as a "Fab region". A Fc region has an effector function to initiate a reaction after an antibody binds to an antigen, and a Fab region has a function to bind to an antigen. A Fab region and Fc region of a heavy chain are bound to each other through a hinge part. Papain, which is a proteolytic enzyme and which is contained in papaya, decomposes a hinge part to cut into two Fab regions and one Fc region. The part close to the tip of the "Y" shape in a Fab region is referred to as a "variable region (V region)", since there are various changes in the amino acid sequence in order to bind to various antigens. A variable region of a light chain is referred to as a "VL region", and a variable region of a heavy chain is referred to as a "VH region". A Fc region and the other part in a Fab region except for a V region are referred to as a "constant region (C region)", since there is relatively less change. A constant region of a light chain is referred to as a "CL region", and a constant region of a heavy chain is referred to as a "CH region". A CH region is further classified into three regions of CH1 to CH3. A Fab region of a heavy chain is composed of a VH region and CH1, and a Fc region of a heavy chain is composed of CH2 and CH3. There is a hinge part between CH1 and CH2. Protein L binds to a variable region of which a light chain is κ chain (Non-patent Documents 5 to 7), and the variable region is sometimes abbreviate to "VL-κ" in the present disclosure.

The κ chain variable region-binding peptide according to one or more embodiments of the present invention binds to a κ chain variable region of an immunoglobulin, i.e. VL-κ region. A VL-κ chain variable region-containing protein, to which the peptide according to one or more embodiments, binds may contain a VL-κ region, and may be IgG containing both of a Fab region and a Fc region, other Ig such as IgM, IgD and IgA, or an immunoglobulin derivative prepared by mutating such Ig using protein engineering. Such an immunoglobulin molecule derivative to be bound by the VL-κ chain variable region-binding peptide according to one or more embodiments of the present invention is not particularly restricted as long as the derivative contains a VL-κ chain variable region. For example, the derivative is exemplified by a Fab fragment which is fragmented to only a Fab region of an immunoglobulin G, scFv consisting of only a variable region of an immunoglobulin G, a chimera immunoglobulin G prepared by replacing a part of domains of a human immunoglobulin G with a domain of an immunoglobulin G derived from other organism to be fused, an immunoglobulin G of which a sugar chain in a Fc region is subjected to molecular alteration, and a scFv fragment to which a drug covalently binds.

In one or more embodiments of the present invention, the term "peptide" means any molecules having a polypeptide structure. In the range of the "peptide", not only a so-called protein but also a fragmented peptide and a peptide to which other peptide is bound through a peptide bond are included. The term "domain" means a unit of higher-order structure of a protein. A domain is composed of from dozens to hundreds of amino acid residues, and means a peptide unit which can sufficiently serve some kind of a physicochemical or biochemical function. The term "mutant" of a protein or peptide means a protein or peptide obtained by introducing at least one substitution, addition or deletion of an amino acid into a sequence of a wild protein or peptide. A mutation to substitute an amino acid is described by adding a wild or non-mutated amino acid residue before the number of a substituted position and adding a mutated amino acid residue after the number of the substituted position. For example, the mutation to substitute Gly at $29^{th}$ position by Ala is described as G29A.

The affinity separation matrix according to one or more embodiments of the present invention contains a water-insoluble base material and a ligand. The term "water-insoluble carrier" in one or more embodiments of the present invention exhibits insolubility against an aqueous solvent in a peptide solution, and contains an immobilized ligand so that the carrier can be used for purifying a peptide which specifically binds to the ligand.

A water-insoluble base material usable in one or more embodiments of the present invention is exemplified by an inorganic base material such as glass beads and silica gel; an organic base material composed of a synthetic polymer such as cross-linked polyvinyl alcohol, cross-linked polyacrylate, cross-linked polyacrylamide and cross-linked polystyrene or a polysaccharide such as crystalline cellulose, cross-linked cellulose, cross-linked agarose and cross-linked dextran; and a composite base material obtained from the combination of the above base materials, such as an organic-organic composite base material and an organic-inorganic composite base material. The commercial product thereof is exemplified by porous cellulose gel GCL2000, Sephacryl S-1000 prepared by crosslinking allyl dextran and methylene bisacrylamide through a covalent bond, an acrylate base material Toyopearl, a cross-linked agarose base material Sepharose CL4B, and a cross-linked cellulose base material Cellufine. However, it should be noted that the water-insoluble base material usable in one or more embodiments of the present invention is not restricted to the base materials exemplified as the above.

The water-insoluble base material usable in one or more embodiments of the present invention may have large surface area and that the base material is porous with a large number of fine pores having a suitable size in terms of a purpose and method for using the affinity separation matrix according to one or more embodiments of the present invention. The base material may have any form such as beads, monolith, fiber and film (including hollow fiber), and any form can be selected.

The term "ligand" in one or more embodiments of the present invention means a substance and a functional group to selectively bind to or adsorb a target molecule from an aggregate of molecules on the basis of a specific affinity between molecules, such as binding between an antigen and an antibody, and means the peptide which specifically binds to an immunoglobulin in one or more embodiments of the present invention. In one or more embodiments of the present invention, the term "ligand" also means an "affinity ligand".

In one or more embodiments of the present invention, the peptide is used as an affinity ligand which is characterized in having an affinity for an immunoglobulin or a fragment thereof, particularly a VL-κ region. An affinity separation matrix obtained by immobilizing the ligand on a water-insoluble base material is also similarly included in one or more embodiments of the present invention as one embodiment.

The ligand used in one or more embodiments of the present invention is an antibody κ chain variable region-binding peptide containing B5 domain of Protein L derived from *Peptostreptococcus magnus* 312 strain or a part thereof.

Protein L (PpL) is a protein derived from a cell wall of an anaerobic gram-positive coccus classified in *Peptostreptococcus*. In one or more embodiments of the present invention, the PpL derived from *Peptostreptococcus magnus* may be used, two kinds of PpLs derived from *Peptostreptococcus magnus* 312 strain and *Peptostreptococcus magnus* 3316 strain may be used, and the PpL derived from 312 strain may be used. In the present disclosure, PpL derived from *Peptostreptococcus magnus* 312 strain is sometimes abbreviated to "PpL312" and PpL derived from *Peptostreptococcus magnus* 3316 strain is sometimes abbreviated to "PpL3316". The amino acid sequence of PpL312 is SEQ ID NO: 1, and the amino acid sequence of PpL3316 is SEQ ID NO: 2, which SEQ ID NOs contain a signal sequence.

PpL contains a plurality of VL-κ-binding domains consisting of 70 to 80 residues. The number of VL-κ-binding domains in PpL312 is 5, and the number of VL-κ-binding domains in PpL3316 is 4. Each of VL-κ-binding domains of PpL312 are referred to as B1 domain (SEQ ID NO: 3), B2 domain (SEQ ID NO: 4), B3 domain (SEQ ID NO: 5), B4 domain (SEQ ID NO: 6) and B5 domain (SEQ ID NO: 7) in the order from the N-terminal, and each of VL-κ-binding domains of PpL3316 are referred to as C1 domain (SEQ ID NO: 8), C2 domain (SEQ ID NO: 9), C3 domain (SEQ ID NO: 10) and C4 domain (SEQ ID NO: 11) in the order from the N-terminal. The amino acid sequence of B5 domain of PpL 312 may be the amino acid sequence of SEQ ID NO: 7.

It has been found from a research that about 20 residues at the N-terminal part of a VL-κ-binding domain do not form a specific secondary structure; and even when the N-terminal region is deleted, the three-dimensional structure and the VL-κ binding property of a VL-κ-binding domain is maintained (Non-patent Document 7). As a result, for example, peptides having the amino acid sequence of SEQ ID NO: 12 with respect to B1 domain, the amino acid sequence of SEQ ID NO: 13 with respect to B2 domain, the amino acid sequence of SEQ ID NO: 14 with respect to B3 domain, the amino acid sequence of SEQ ID NO: 15 with respect to B4 domain, the amino acid sequence of SEQ ID NO: 16 with respect to B5 domain, the amino acid sequence of SEQ ID NO: 17 with respect to C1 domain, the amino acid sequence of SEQ ID NO: 18 with respect to C2 domain, the amino acid sequence of SEQ ID NO: 19 with respect to C3 domain and the amino acid sequence of SEQ ID NO: 20 with respect to C4 domain function as a VL-κ-binding domain. The amino acid sequence of the B5 domain of PpL312 in the present disclosure may be SEQ ID NO: 16.

The amino acid sequence corresponding to the amino acid sequences of SEQ ID NOs: 1 and 2 with the deletion of some residues at the N-terminal and/or C-terminal is also included in one or more embodiments of the present invention range. The number of the deleted residues may be 1 or more and 5 or less, 1 or more and 4 or less, 1 or more and 3 or less, 1 or 2, or 1.

In one or more embodiments of the present invention, the phrase, a peptide "has a (specific) amino acid sequence", means that the specific amino acid sequence is contained in the amino acid sequence of the peptide and the function of the peptide is maintained. The sequence of a peptide other than a specific amino acid sequence is exemplified by a signal peptide, histidine tag, a linker sequence for immobilization, and a crosslinking structure such as disulfide bond.

As one of the embodiments, a fusion peptide characterized in that the VL-κ region-binding peptide according to one or more embodiments of the present invention is fused with other peptide having a different function as one component is exemplified. The other peptide is exemplified by albumin, glutathione S-transferase, i.e. GST, a signal peptide and histidine tag, but is not restricted to the examples. In addition, peptides fused with a nucleic acid such as DNA aptamer, a drug such as an antibiotic or a polymer such as PEG, i.e. polyethylene glycol, are also included in the range of one or more embodiments of the present invention as long as the availability of the peptide of one or more embodiments of the present invention is utilized in a fusion peptide.

The amino acid sequence of the above-described antibody κ chain variable region-binding peptide is specifically exemplified by the following amino acid sequences (1) to (3):

(1) an amino acid sequence of SEQ ID NO: 7 or SEQ ID NO: 16;

(2) an amino acid sequence of SEQ ID NO: 7 or SEQ ID NO: 16 with deletion, substitution and/or addition of 1 or more and 10 or less amino acid residues, having a binding capability to an antibody κ chain variable region;

(3) an amino acid sequence with a sequence identity of 85% or more to the amino acid sequence of SEQ ID NO: 7 or SEQ ID NO: 16, having a binding capability to an antibody κ chain variable region.

The number of the deletion and the like in the above-described amino acid sequence (2) according to one or more embodiments of the present invention may be 8 or less, 6 or less, 5 or less, 4 or less, or 3 or less, 2 or less, or 1.

The term "sequence identity" in the phrase "amino acid sequence with a sequence identity of 85% or more to the amino acid sequence specified in the (1)" in the above-described amino acid sequence (3) according to one or more embodiments of the present invention is not particularly restricted as long as the peptide having the sequence identity of the amino acid sequence has a binding capability to an antibody κ chain variable region. The sequence identity of the amino acid sequence is not particularly restricted as long as the sequence identity is 85% or more, 86% or more, 88% or more, or 90% or more, 92% or more, 94% or more, 95% or more, 96% or more, 98% or more, or 99% or more, 99.5% or more, or 99.8% or more. The term "sequence identity" in one or more embodiments of the present invention means a similarity degree between 2 or more amino acid sequences. Accordingly, when a homology between 2 amino acid sequences is higher, a similarity of the sequences is higher. It can be evaluated by directly comparing the sequences with each other, and specifically confirmed by using a program for amino acid sequence multiple alignment: Clustal (http://www.clustal.org/omega/) or commercially available sequence analysis software whether 2 kinds of amino acid sequences has a specific homology or not.

For example, the phrase "having a binding capability to an antibody κ chain variable region" in the above-described amino acid sequences (2) and (3) means that an affinity for IgG-Fab is improved in comparison with at least a control in the affinity evaluation test for IgG-Fab using a biosensor in Example 2(2) described later.

The amino acid sequence of the antibody κ chain variable region-binding peptide used in one or more embodiments of the present invention is specifically exemplified by the amino acid sequence of SEQ ID NO: 7 wherein the $17^{th}$ position is glutamic acid, the $19^{th}$ position is isoleucine, the $20^{th}$ position is tyrosine, the $22^{nd}$ position is glutamic acid, the $25^{th}$ position is threonine, the $26^{th}$ position is valine, the $30^{th}$ position is threonine, the $50^{th}$ position is serine and the $53^{rd}$ position is histidine, and the amino acid sequence of SEQ ID NO: 16 wherein the $7^{th}$ position is glutamic acid, the $9^{th}$ position is isoleucine, the $10^{th}$ position is tyrosine, the $12^{nd}$ position is glutamic acid, the $15^{th}$ position is threonine, the $16^{th}$ position is valine, the $20^{th}$ position is threonine, the $40^{th}$ position is serine and the $43^{rd}$ position is histidine.

PpL is a protein which contains 4 or 5 VL-κ region-binding domains in the form of tandem line. As one of the embodiments, the VL-κ region-binding peptide according to one or more embodiments of the present invention may be a multimer of 2 or more monomers or single domains of the VL-κ region-binding peptide connected each other. The number of the monomers or single domains may be 3 or more, 4 or more, or 5 or more. With respect to the upper limit of the number of connected domains, the number may be 10 or less, 8 or less, or 6 or less. Such a multimer may be a homomultimer in which one kind of VL-κ region-binding peptides are connected, such as homodimer and homotrimer, or a heteromultimer in which two or more kinds of VL-κ region-binding peptides are connected, such as heterodimer and heterotrimer, on the proviso that the heteromer does not contain any one of B1 to B4 domain of PpL312 and C1 to C4 domain of PpL3316.

A method for connection between monomer peptides according to one or more embodiments of the present invention is exemplified by a connecting method through one or more amino acid residues and a directly connecting method without an amino acid residue, but is not restricted thereto. The number of the amino acid residue for connection is not particularly restricted, and may be 20 residues or less, 15 residues or less, 10 residues or less, 5 residues or less, or 2 residues or less. The amino acid residue for connection may not destabilize a three dimensional structure of a monomer peptide.

In the affinity separation matrix according to one or more embodiments of the present invention, the above-described ligand is immobilized on the water-insoluble base material.

The above-described ligand is covalently immobilized on the above-described water-insoluble base material directly or through a linker group. The linker group is exemplified by a $C_{1-6}$ alkylene group, an amino group (—NH—), an ether group (—O—), a carbonyl group (—C(=O)—), an ester group (—C(=O)O— or —OC(=O)—), an amide group (—C(=O)NH— or —NHC(=O)—), a urea group (—NHC(=O)NH—); a group formed by connecting 2 or more and 10 or less groups selected from the group consisting of a $C_{1-6}$ alkylene group, an amino group, an ether group, a carbonyl group, an ester group, an amide group and a urea group; a $C_{1-6}$ alkylene group having a group selected from the group consisting of an amino group, an ether group, a carbonyl group, an ester group, an amide group and a urea group on one or both of ends. The above-described number of the connected groups may be 8 or less, 6 or less, 5 or less, or 4 or less. The above-described $C_{1-6}$ alkylene group may be substituted by a substituent such as a hydroxy group.

The affinity separation matrix according to one or more embodiments of the present invention can be produced by immobilizing the ligand on the water-insoluble base material.

With respect to a method for immobilizing the ligand, for example, the ligand can be bound to a base material by a conventional coupling method utilizing an amino group, a carboxy group or a thiol group of the ligand. Such a coupling method is exemplified by an immobilization method including activation of a base material by a reaction with cyanogen bromide, epichlorohydrin, diglycidyl ether, tosyl chloride, tresyl chloride, hydrazine, sodium periodate or the like, or introduction of a reactive functional group on the base material surface, and the coupling reaction between the resulting base material and a compound to be immobilized as a ligand; and an immobilization method by condensation and crosslinking which method includes adding a condensation reagent such as carbodiimide or a reagent having a plurality of functional groups in the molecule, such as glutaraldehyde, into a mixture containing a base material and a compound to be immobilized as a ligand.

A spacer molecule may be introduced between the ligand and base material. Alternatively, the ligand may be directly immobilized on the base material. Accordingly, the VL-κ region-binding peptide according to one or more embodiments of the present invention may be chemically modified for immobilization, or may have an additional amino acid residue useful for immobilization. Such an amino acid useful for immobilization is exemplified by an amino acid having a functional group useful for a chemical reaction for immobilization in a side chain, and specifically exemplified by Lys having an amino group in a side chain and Cys having a thiol group in a side chain. Since the binding capability of the peptide according to one or more embodiments of the present invention to a VL-κ region is principally maintained in a matrix prepared by immobilizing the peptide as a ligand in one or more embodiments of the present invention, any modification and change for immobilization are included in the range of one or more embodiments of the present invention.

It becomes possible by using the affinity separation matrix of one or more embodiments of the present invention that a peptide containing a κ chain variable region of an immunoglobulin G, i.e. VL-κ-containing protein, is purified in accordance with affinity column chromatography purification method. A VL-κ-containing protein can be purified by a procedure in accordance with a method for purifying an immunoglobulin by affinity column chromatography, for example, such as a method using SpA affinity separation matrix (Non-Patent Document 1).

The method for producing a VL-κ-containing protein according to one or more embodiments of the present invention is characterized in comprising the steps of contacting the affinity separation matrix with a liquid sample comprising the VL-κ-containing protein and separating the protein bound to the affinity separation matrix from the affinity separation matrix.

Specifically, after a buffer which contains a VL-κ-containing protein and of which pH is approximately neutral is prepared, the solution is allowed to pass through an affinity column packed with the affinity separation matrix of one or more embodiments of the present invention so that the VL-κ-containing protein is adsorbed. Then, an appropriate amount of a pure buffer is allowed to pass through the affinity column to wash the inside of the column. At the time, the target VL-κ-containing protein is still adsorbed on the affinity separation matrix of one or more embodiments of the present invention in the column. The affinity separation matrix is excellent in the absorption and retention performance of a target VL-κ-containing protein from the step of adding a sample through the step of washing the matrix. Then, an acid buffer of which pH is appropriately adjusted is allowed to pass through the column to elute the target VL-κ-containing protein. As a result, purification with high purity can be achieved. Into the acid buffer used for eluting the peptide, a substance for promoting dissociation from the matrix may be added.

The affinity separation matrix according to one or more embodiments of the present invention can be reused by allowing an adequate strong acid or strong alkaline pure buffer which do not completely impair the function of the ligand compound or the base material of a carrier to pass through the matrix for washing. In the buffer for reuse, an adequate modifying agent or an organic solvent may be added.

One or more embodiments of the present invention also relate to a DNA encoding the above-described antibody κ chain variable region-binding peptide. The DNA encoding the peptide of one or more embodiments of the present invention may be any DNA as long as the amino acid sequence produced from translation of the base sequence of the DNA constitutes the peptide. The base sequence is exemplified by the base sequence of SEQ ID NO: 21. Such a base sequence can be obtained by common known techniques, for example, using polymerase chain reaction (hereinafter, abbreviated as "PCR") technology. Alternatively, such abase sequence can be synthesized by publicly-known chemical synthesis techniques or is available from DNA libraries. A codon in the base sequence may be substituted by a degenerate codon, and the base sequence is not necessarily the same as the original base sequence as long as the translated amino acids are the same as those encoded by the original base sequence. It is possible to obtain a recombinant DNA having the one or more base sequences, a vector containing the recombinant DNA, such as a plasmid or a phage, a transgenic microorganism or cell transformed by the vector having the DNA, a genetically engineered organisms having the DNA introduced therein, or a cell-free protein synthesis system using the DNA as a template for transcription.

The VL-κ region-binding peptide according to one or more embodiments of the present invention may be obtained as a fusion peptide fused with a publicly-known protein which beneficially has an action to assist the expression of the protein or to facilitate the purification of the protein. In other words, it is possible to obtain a microorganism or cell containing at least one recombinant DNA encoding a fusion peptide containing the VL-κ region-binding peptide according to one or more embodiments of the present invention. The above-described protein is exemplified by a maltose-binding protein (MBP) and a glutathione S-transferase (GST), but is not restricted to the exemplified proteins.

Site-specific mutagenesis for modifying the DNA encoding the peptide according to one or more embodiments of the present invention can be carried out using recombinant DNA technology, PCR method or the like as follows.

A mutagenesis by recombinant DNA technology can be carried out as follows: in the case where there are suitable restriction enzyme recognition sequences on both sides of a target mutagenesis site in the gene encoding the peptide according to one or more embodiments of the present invention, cassette mutagenesis method can be carried out in which method a region containing the target mutagenesis site is removed by cleaving the restriction enzyme recognition sites with the above-described restriction enzymes and then a mutated DNA fragment is inserted. Into the mutated DNA fragment, mutation is introduced only at the target site by a method such as chemical synthesis.

For example, site-directed mutagenesis by PCR can be carried out by double primer mutagenesis. In double primer mutagenesis, PCR is carried out by using a double-stranded plasmid encoding the peptide according to one or more embodiments of the present invention as a template, and using two kinds of synthesized oligo primers which contain complementary mutations in the + strand and − strand.

A DNA encoding a multimer peptide can be produced by ligating the desired number of DNAs each encoding the monomer peptide (single domain) according to one or more embodiments of the present invention to one another in tandem. For example, with respect to a connecting method for the DNA encoding the multimer peptide, a suitable restriction enzyme site is introduced in the DNA sequence, and double-stranded DNA fragments cleaved with a restriction enzyme are ligated using a DNA ligase. One restriction enzyme site may be introduced or a plurality of restriction enzyme sites of different types may be introduced. When the base sequences encoding each monomer peptide in the DNA encoding the multimer peptide are the same, homologous recombination may be possibly induced in a host. Thus, the sequence identity between base sequences of DNAs encoding the monomer peptides to be connected may be 90% or less, 85% or less, 80% or less, or 75% or less. The identity of a base sequence can be also determined by an ordinary method similarly to an amino acid sequence.

The "expression vector" of one or more embodiments of the present invention includes a base sequence encoding the above-described peptide of one or more embodiments of the present invention or a part of the amino acid sequence of the peptide, and a promoter that can be operably linked to the base sequence to function in a host. Usually, the vector can be constructed by linking or inserting a gene encoding the peptide of one or more embodiments of the present invention to a suitable vector. The vector for insertion of the gene is not particularly restricted as long as the vector is capable of autonomous replication in a host. As such a vector, a plasmid DNA or a phage DNA can be used. For example, in the case of using *Escherichia coli* as a host, a pQE series vector (manufactured by QIAGEN), a pET series vector (manufactured by Merck), a pGEX series vector (manufactured by GE Healthcare Bioscience) or the like can be used.

The transformant of one or more embodiments of the present invention can be produced by introducing the recombinant vector of one or more embodiments of the present invention into a host cell. A method for introducing the recombinant DNA into a host is exemplified by a method using a calcium ion, electroporation method, spheroplast method, lithium acetate method, *agrobacterium* infection method, particle gun method and polyethylene-glycol method, but is not restricted thereto. A method for expressing the function of the obtained gene in a host is also exemplified by a method in which the gene according to one or more embodiments of the present invention is implanted into a genome (chromosome). A host cell is not particularly restricted, and bacteria (eubacteria) such as *Escherichia coli, Bacillus subtilis, Brevibacillus, Staphylococcus, Streptococcus, Streptomyces* and *Corynebacterium* may be used in terms of mass production in a low cost.

The VL-κ region-binding peptide according to one or more embodiments of the present invention can be produced by cultivating the above-described transformant in a culture medium, allowing the transformant to express and accumulate the peptide of one or more embodiments of the present invention in the cultivated bacterial cell (including the periplasmic space of the bacterial cell) or in the culture medium (outside the bacterial cell), and collecting the desired peptide from the culture. Further, the peptide of one or more embodiments of the present invention can also be produced by cultivating the above-described transformant in a culture medium, allowing the transformant to express and accumulate the fusion protein containing the peptide of one or more embodiments of the present invention in the cultivated bacterial cell (including the periplasmic space of the bacterial cell) or in the culture medium (outside the bacterial cell), collecting the fusion peptide from the culture, cleaving the fusion peptide with a suitable protease, and collecting the desired peptide.

The transformant of one or more embodiments of the present invention can be cultivated in a culture medium in accordance with a common method for cultivating a host cell. The culture medium used for cultivating the obtained transformant is not particularly restricted as long as the culture medium enables high yield production of one or more embodiments of the present invention peptide with high efficiency. Specifically, carbon source and nitrogen source, such as glucose, sucrose, glycerol, polypeptone, meat extract, yeast extract and casamino acid can be used. In addition, an inorganic salt such as potassium salt, sodium salt, phosphate, magnesium salt, manganese salt, zinc salt andiron salt is added as required. In the case of an auxotrophic host cell, a nutritional substance necessary for the growth thereof may be added. In addition, an antibiotic such as penicillin, erythromycin, chloramphenicol and neomycin may be added as required.

Furthermore, in order to inhibit the degradation of the target peptide caused by a host-derived protease present inside or outside the bacterial cell, a publicly-known protease inhibitor and/or other commercially available protease inhibitor may be added in an appropriate concentration. The publicly-known protease inhibitor is exemplified by phenylmethane sulfonyl fluoride (PMSF), benzamidine, 4-(2-aminoethyl)-benzenesulfonyl fluoride (AEBSF), antipain, chymostatin, leupeptin, Pepstatin A, phosphoramidon, aprotinin and ethylenediaminetetraacetic acid (EDTA).

In order to obtain rightly folded VL-κ region-binding peptide according to one or more embodiments of the present invention, for example, a molecular chaperone such as GroEL/ES, Hsp70/DnaK, Hsp90 and Hsp104/ClpB may be used. For example, such a molecular chaperone is co-existed with the peptide according to one or more embodiments of the present invention by coexpression or as a fusion protein. As a method for obtaining rightly folded peptide according to one or more embodiments of the present invention, addition of an additive for assisting right folding into the culture medium and cultivating at a low temperature are exemplified, but the method is not restricted thereto.

The culture medium for cultivating transformant produced from an *Escherichia coli* as a host is exemplified by LB medium containing triptone 1%, yeast extract 0.5% and NaCl 1%, 2×YT medium containing triptone 1.6%, yeast extract 1.0% and NaCl 0.5%, or the like.

For example, the transformant may be aerobically cultivated in an aeration-stirring condition at a temperature of 15 to 42° C., or 20 to 37° C., for from several hours to several days. As a result, the peptide of one or more embodiments of the present invention is accumulated in the cultivated cell (including the periplasmic space of the cell) or in the culture medium (outside the cell) to be recovered. In some cases, the cultivation may be performed anaerobically without aeration. In the case where a recombinant peptide is secreted, the produced recombinant peptide can be recovered after the cultivation period by separating the supernatant containing the secreted peptide using a common separation method such as centrifugation and filtration from the cultured cell. In addition, in the case where the peptide is accumulated in the cultivated cell (including the periplasmic space), the peptide accumulated in the cell can be recovered, for example, by collecting the bacterial cell from the culture medium by centrifugation, filtration or the like, and then disrupting the bacterial cell by sonication method, French press method or the like, and/or solubilizing the bacterial cell by adding a surfactant or the like.

A method for purifying the peptide according to one or more embodiments of the present invention can be carried out by any one or an appropriate combination of techniques such as affinity chromatography, cation or anion exchange chromatography, gel filtration chromatography and the like. It can be confirmed whether the obtained purified substance is the target peptide or not by an ordinary method such as SDS polyacrylamide gel electrophoresis, N-terminal amino acid sequence analysis and Western blot analysis.

The present application claims the benefit of the priority date of Japanese patent application No. 2015-12663 filed on Jan. 26, 2015. All of the contents of the Japanese patent application No. 2015-12663 filed on Jan. 26, 2015, are incorporated by reference herein.

EXAMPLES

Hereinafter, one or more embodiments of the present invention are described in more detail with Examples. However, the present invention is not restricted to the following Examples.

The mutant peptide obtained in the following Examples is described as "peptide name—introduced mutation", and wild type into which mutation is not introduced is described as "peptide name—Wild". For example, B5 domain of wild PpL312 having SEQ ID NO: 7 is described as "LB5-Wild". A protein composed of a plurality of single domains connected each other is represented by adding a connection number and "d" after a period. For example, a single domain is described as "1d". In addition, in the following Examples, B5 domain of PpL312 having SEQ ID NO: 16 with the deletion of the N-terminal region was mainly used in the experiment. It has been known that the N-terminal region does not build a secondary structure. The peptide is represented as "LB5t-Wild" to be distinguished from SEQ ID NO: 7.

Example 1: Preparation of LB5t-Wild.1d, B5 Domain of PpL 312 with Deletion of N-Terminal Region (1) Preparation of Expression Plasmid A base sequence of SEQ ID NO: 21 encoding LB5t-Wild.1d was designed by reverse translation from the amino acid sequence of SEQ ID NO: 16. The method for producing the expression plasmid is shown in FIG. 1. The DNA encoding LB5t-Wild.1d was prepared by ligating two kinds of double-stranded DNAs (f1 and f2) having the same restriction enzyme site, and integrated into the multiple cloning site of an expression vector. In fact, the preparation of the peptide-coding DNA and the integration into the vector were simultaneously performed by ligating three fragments for connecting three double-stranded DNAs of the two kinds of double-stranded DNAs and an expression vector. The two kinds of double-stranded DNAs were prepared by elongating two kinds of single-stranded DNAs (f1-1/f1-2 or f2-1/f2-2) respectively containing about 30-base complementary region with overlapping PCR. Hereinafter, the specific experimental procedure is described. Single-stranded oligo DNAs f1-1 (SEQ ID NO: 22)/f1-2 (SEQ ID NO: 23) were synthesized by outsourcing to Sigma Genosys. The overlapping PCR was performed using Pyrobest (manufactured by Takara Bio, Inc.) as a polymerase. The PCR product was subjected to agarose electrophoresis and the target band was cut out to extract the double-stranded DNA. The thus extracted double-stranded DNA was cleaved with the restriction enzymes BamHI and HindIII (both available from Takara Bio, Inc.). Similarly, single-stranded oligo DNAs f2-1 (SEQ ID NO: 24)/f2-2 (SEQ ID NO: 25) were synthesized by outsourcing. The double-stranded DNA synthesized by overlapping PCR was extracted and cleaved with the restriction enzymes HindIII and EcoRI (both available from Takara Bio, Inc.). Then, the two kinds of double-stranded DNAs were sub-cloned into the BamHI/EcoRI site in the multiple cloning site of a plasmid vector pGEX-6P-1 (GE Healthcare Bioscience). The ligation reaction for the subcloning was performed using Ligation high (manufactured by TOYOBO CO., LTD.) in accordance with the protocol attached to the product.

A competent cell ("*Escherichia coli* HB101" manufactured by Takara Bio, Inc.) was transformed using the above-described plasmid vector pGEX-6P-1 in accordance with the protocol attached to the competent cell product. By using the plasmid vector pGEX-6P-1, LB5t-Wild.1d which was fused with glutathione-S-transferase (hereinafter, abbreviated as "GST") could be produced. Then, the plasmid DNA was amplified and extracted using a plasmid purification kit ("Wizard Plus SV Minipreps DNA Purification System" manufactured by Promega) in accordance with the standard protocol attached to the kit. The base sequence of the coding DNA of the expression plasmid was determined by using a DNA sequencer ("3130xl Genetic Analyzer" manufactured by Applied Biosystems). The sequencing PCR was performed by using a gene analysis kit ("BigDye Terminator v. 1.1 Cycle Sequencing Kit" manufactured by Applied Biosystems) and DNA primers for sequencing the plasmid vector pGEX-6P-1 (manufactured by GE Healthcare Bioscience) in accordance with the attached protocol. The sequencing product was purified by using a plasmid purification kit ("BigDye XTerminator Purification Kit" manufactured by Applied Biosystems) in accordance with the attached protocol and used for the base sequence analysis.

(2) Production and Purification of Protein

The transformant produced by integrating LB5t-Wild.1d gene obtained in the above-described (1) was cultivated in 2×YT medium containing ampicillin at 37° C. overnight. The culture solution was inoculated in 2×YT medium containing about 100-fold amount of ampicillin for cultivation at 37° C. for about 2 hours. Then, isopropyl-1-thio-β-D-galactoside, which is hereinafter abbreviated to IPTG, was added so that the final concentration thereof became 0.1 mM, and the transformant was further cultivated at 37° C. for 18 hours.

After the cultivation, the bacterial cell was collected by centrifugation and re-suspended in 5 mL of PBS buffer. The cell was broken by sonication and centrifuged to separate a supernatant fraction as a cell-free extract from an insoluble fraction. When a target gene is integrated into the multiple cloning site of pGEX-6P-1 vector, a fusion peptide having GST added to the N-terminal is produced. Each fraction was analyzed by SDS electrophoresis; as a result, a peptide band assumed to be induced by IPTG was detected at a position corresponding to a molecular weight of about 25,000 or more in the cases of each of all the cell-free extracts obtained from all of the cultured solutions of each transformant.

The GST fusion peptide was roughly purified from each of the cell-free extract containing the GST fusion peptide by affinity chromatography using a GSTrap FF column (GE Healthcare Bioscience), which had an affinity for GST. Specifically, each of the cell-free extract was added to the GSTrap FF column and the column was washed with a standard buffer (20 mM NaH$_2$PO$_4$—Na$_2$HPO$_4$, 150 mM NaCl, pH 7.4). Then, the target GST fusion peptide was eluted by using an elution buffer (50 mM Tris-HCl, 20 mM Glutathione, pH 8.0).

When a gene is integrated into the multiple cloning site of pGEX-6P-1 vector, an amino acid sequence by which GST can be cleaved using sequence-specific protease: PreScission Protease (manufactured by GE Healthcare Bioscience) is inserted between GST and a target protein. By using such PreScission Protease, GST was removed in accordance with the attached protocol. The target peptide was purified by gel filtration chromatography using a Superdex 75 10/300 GL column (manufactured by GE Healthcare Bioscience) from the GST-removed sample used for assay. Each of the reaction mixture was added to the Superdex 75 10/300 GL column equilibrated with a standard buffer, and the target protein therein was separated and purified from the removed GST and PreScission Protease.

The above-described all of the peptide purification by chromatography using the column were performed by using AKTAprime plus system (manufactured by GE Healthcare Bioscience). In addition, after the removal of GST, the sequence of Gly-Pro-Leu-Gly-Ser derived from the vector pGEX-6P-1 was added at the N-terminal side of the protein produced in the present example.

Example 2: Evaluation of Affinity of LB5t-Wild.1d for IgG-Fab (1) Preparation of Fab Fragment Derived from IgG (IgG-Fab)

A humanized monoclonal IgG product as a raw material was fragmented into a Fab fragment and a Fc fragment using papain, and only the Fab fragment was separated and purified. In the experiment, 6 kinds of Fabs were prepared. With respect to each Fab, name, humanized monoclonal IgG product as a raw material and the like are described in Table 1.

TABLE 1

| | | | | |
|---|---|---|---|---|
| | Prepared Fab name: | aRSV-Fab | aTNFa-Fab | aEGFR-Fab |
| Entire length antibody (Raw material) | Subsatance name: Product name: Manufacturer/seller: Basic structure: PpL connection part: | Palivizumab Synagis AbbVie humanized antibody/IgG1κ Human VLκ sub: 1 | Infliximab Remicade Mitsubishi Tanabe Pharma chimeric antibody/IgG1κ Mouse VLκ sub: 5 | Cetuximab Erbitux Merck Serono chimeric antibody/IgG1κ Mouse VLκ sub: 5 |
| | Prepared Fab name: | aHER2-Fab | aIgE-Fab | aRANKL-Fab |
| Entire length antibody (Raw material) | Subsatance name: Product name: Manufacturer/seller: Basic structure: PpL connection part: | Trastuzumab Herceptin Chugai pharmaceutical humanized antibody/IgG1κ Human VLκ sub: 1 | Omalizumab Xolair Novartis humanized antibody/IgG1κ Human VLκ sub: 1 | Denosumab Pralia Daiichi Sankyo humanized antibody/IgG2κ Human VLκ sub: 3 |

Hereinafter, a method for producing IgG-Fab derived from anti-RSV monoclonal antibody (general name: Palivizumab) is representatively described. In the present disclosure, when other IgG-Fab was used for the evaluation, the other IgG-Fab was prepared basically by a similar method. Specifically, a humanized monoclonal IgG product was dissolved in a buffer for papain treatment (0.1 M AcOH—AcONa, 2 mM EDTA, 1 mM cysteine, pH 5.5), and agarose on which papain was immobilized ("Papain Agarose from papaya latex" manufactured by SIGMA) was added thereto. The mixture was incubated with stirring by a rotator at 37° C. for about 8 hours. The IgG-Fab was purified by recovering as a flow-through fraction in an affinity chromatography using MabSelect SuRe column (manufactured by GE Healthcare Bioscience) from the reaction mixture which contained both of a Fab fragment and a Fc fragment and which was separated from the agarose on which papain was immobilized. The obtained IgG-Fab solution was subjected to purification by gel filtration chromatography using Superdex 75 10/300 GL column to obtain the solution of IgG-Fab (aRSV-Fab). In the chromatography, a standard buffer was used for equilibration and separation. Similarly to the above-described Example 1, AKTAprime plus system was used in the chromatography for protein purification.

(2) Analysis of Affinity of LB5t-Wild.1d for IgG-Fab

The affinity of LB5t-Wild.1d obtained in the above Example 1(2) for totally 6 kinds of IgG-Fabs was evaluated using a biosensor Biacore 3000 (manufactured by GE Healthcare Bioscience) utilizing surface plasmon resonance. In the present example, the IgG-Fab obtained in the above Example 2(1) was immobilized on a sensor tip, and each of the peptide was flown on the tip to detect the interaction between the two. The IgG-Fab was immobilized on a sensor tip CM5 by amine coupling method using N-hydroxysuccinimide (NHS) and N-ethyl-N'-(3-dimethylaminopropyl) carbodiimide hydrochloride (EDC), and ethanolamine was used for blocking. All of the sensor tip and reagents for immobilization were manufactured by GE Healthcare Bioscience. The IgG-Fab solution was diluted about 10 times using a buffer for immobilization (10 mM $CH_3COOH$—$CH_3COONa$, pH 4.5), and the IgG-Fab was immobilized on the sensor tip in accordance with the protocol attached to the Biacore 3000. In addition, a reference cell was also prepared by activating another flow cell on the tip with EDC/NHS and then immobilizing human serum albumin (manufactured by Wako Pure Chemical Industries, Ltd.). A peptide solution of LB5t-Wild.1d having concentrations of 0.01, 0.1, 1 or 10 µM was prepared using a running buffer (20 mM $NaH_2PO_4$—$Na_2HPO_4$, 150 mM NaCl, 0.005% P-20, pH 7.4). The peptide solution was added to the sensor tip in a flow rate of 40 µL/min for 1 minute. Bonding response curves at the time of addition (association phase, for 1 minute) and after the addition (dissociation phase, for 1 minute) were sequentially obtained at a measurement temperature of 25° C. After each measurement, the cells were washed using about 20 mM NaOH. The bonding response curve obtained by subtracting the bonding response curve of the reference cell was subjected to fitting analysis by a binding model of 1:1 using a software BIA evaluation attached to the system, and affinity constant ($K_A = k_{on}/k_{off}$) to humanized IgG-Fab was calculated. The result is shown in Table 2.

TABLE 2

| LB5t-Wild.1d | $k_{on}$ (×10$^5$ [M$^{-1}$s]) | $k_{off}$ (×10$^{-2}$ [s$^{-1}$]) | $K_A$ (×10$^6$ [M$^{-1}$]) |
|---|---|---|---|
| aRSV-Fab | 31.2 | 1.7 | 188.0 |
| aTNFa-Fab | 1.5 | 21.5 | 0.7 |
| aEGFR-Fab | 2.3 | 10.4 | 2.2 |
| aHER2-Fab | 5.4 | 1.0 | 56.4 |
| aIgE-Fab | 14.5 | 0.3 | 443.4 |
| aRANKL-Fab | 0.8 | 8.9 | 1.0 |

The experimental result was compared with the binding capability of other VL-κ-binding domains to IgG-Fab. The result with the result of Comparative example 2 is shown as graphs of FIG. 2.

Figure 2:
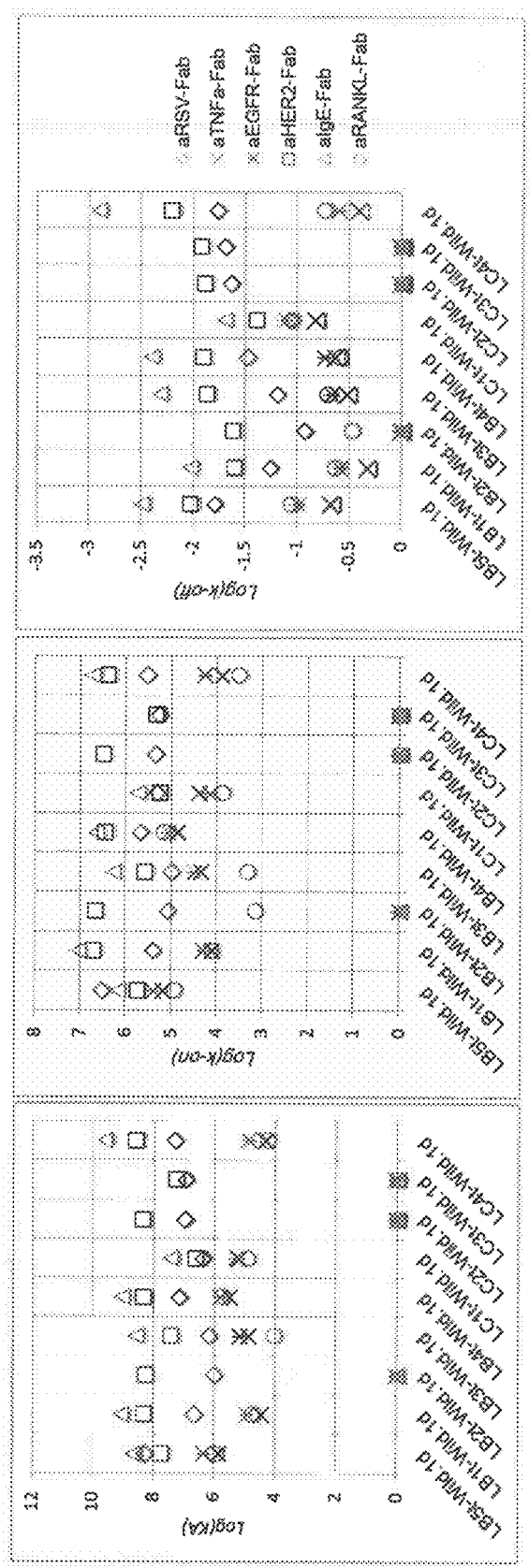
FIG. 2 are graphs prepared by plotting the logarithmic values of an affinity constant ($K_A$), a binding rate constant ($k_{on}$) and a dissociation rate constant ($k_{off}$) of various VL-κ-binding domains of PpL to various IgG-Fabs.

The results shown in Table 2 and FIG. 2, and Table 3 and Table 4 described later, LB5t-Wild.1d exhibited higher binding capability to some Fab such as aRSV-Fab and aTNFa-Fab than other domains. Such a fact has not been known before and can be said to be an astounding result. In particular, B5 domain exhibited the strongest binding capability in the tested peptides to a Fab of which binding capability generally tends to be weak and which cannot bind to some VL-κ-binding domains, such as aTNFa-Fab and aEGFR-Fab. The result indicates the possibility that the affinity separation matrix on which B5 domain or an analogue thereof is immobilized as a ligand enlarges the range of a Fab to be adsorbed.

Comparative Example 1: Preparation of Other VL-κ-Binding Domain of PpL with Deletion of N-Terminal Region The constructs of B1 to B4 and C1 to C4 domains with the deletion of N-terminal region were prepared to be compared with LB5t-Wild.1d, which was B5 domain of PpL312 with the deletion of N-terminal. Each construct name and the amino acid sequence number are described as follows: LB1t-Wild.1d (SEQ ID NO: 12), LB2t-Wild.1d (SEQ ID NO: 13), LB3t-Wild.1d (SEQ ID NO: 14), LB4t-Wild.1d (SEQ ID NO: 15), LC1t-Wild.1d (SEQ ID NO: 17), LC2t-Wild.1d (SEQ ID NO: 18), LC3t-Wild.1d (SEQ ID NO: 19), LC4t-Wild.1d (SEQ ID NO: 20). Solutions of each protein were prepared by preparing an expression plasmid and transformant, cultivating the transformant and purifying the protein similarly to Example 1. A restriction enzyme other than HindIII was used in some cases, but the details are not described.

Comparative Example 2: Evaluation of Affinity of Various VL-κ-Binding Domains with Deletion of N-Terminal Region for IgG-Fab The affinity between various VL-κ-binding domains with the deletion of N-terminal region prepared in Comparative example 1 and 6 kinds of IgG-Fabs prepared in Example 2(1) was evaluated similarly to Example 2(2). The result is shown in Table 3 and Table 4.

TABLE 3

| | $k_{on}$ (×10$^5$ [M$^{-1}$s]) | $k_{off}$ (×10$^{-2}$ [s$^{-1}$]) | $K_A$ (×10$^6$ [M$^{-1}$]) |
|---|---|---|---|
| LB1t-Wild.1d | | | |
| aRSV-Fab | 2.5 | 5.7 | 4.4 |
| aTNFa-Fab | 0.1 | 48.1 | 0.03 |
| aEGFR-Fab | 0.2 | 26.1 | 0.1 |
| aHER2-Fab | 50.9 | 2.5 | 201.2 |
| aIgE-Fab | 107.0 | 1.0 | 1119.2 |
| aRANKL-Fab | 0.1 | 23.3 | 0.1 |
| LB2t-Wild.1d | | | |
| aRSV-Fab | 1.2 | 12.2 | 1.0 |
| aTNFa-Fab | N.D. | N.D. | N.D. |
| aEGFR-Fab | N.D. | N.D. | N.D. |
| aHER2-Fab | 44.9 | 2.5 | 182.5 |
| aIgE-Fab | N.D. | N.D. | N.D. |
| aRANKL-Fab | 0.01 | 34.3 | 0.004 |
| LB3t-Wild.1d | | | |
| aRSV-Fab | 1.0 | 6.7 | 1.4 |
| aTNFa-Fab | 0.2 | 30.5 | 0.1 |
| aEGFR-Fab | 0.3 | 21.9 | 0.1 |
| aHER2-Fab | 3.8 | 1.4 | 28.0 |
| aIgE-Fab | 18.2 | 0.5 | 376.8 |
| aRANKL-Fab | 0.02 | 19.7 | 0.01 |

TABLE 3-continued

| | $k_{on}$ (×10$^5$ [M$^{-1}$s]) | $k_{off}$ (×10$^{-2}$ [s$^{-1}$]) | $K_A$ (×10$^6$ [M$^{-1}$]) |
|---|---|---|---|
| LB4t-Wild.1d | | | |
| aRSV-Fab | 4.7 | 3.4 | 13.8 |
| aTNFa-Fab | 0.7 | 23.9 | 0.3 |
| aEGFR-Fab | 1.1 | 18.7 | 0.6 |
| aHER2-Fab | 27.8 | 1.3 | 220.6 |
| aIgE-Fab | 43.3 | 0.4 | 1077.1 |
| aRANKL-Fab | 1.5 | 26.1 | 0.6 |

TABLE 4

| | $k_{on}$ (×10$^5$ [M$^{-1}$s]) | $k_{off}$ (×10$^{-2}$ [s$^{-1}$]) | $K_A$ (×10$^6$ [M$^{-1}$]) |
|---|---|---|---|
| LB1t-Wild.1d | | | |
| aRSV-Fab | 2.0 | 8.6 | 2.3 |
| aTNFa-Fab | 0.2 | 15.2 | 0.2 |
| aEGFR-Fab | 0.1 | 7.7 | 0.2 |
| aHER2-Fab | 1.8 | 4.1 | 4.3 |
| aIgE-Fab | 5.5 | 2.0 | 27.1 |
| aRANKL-Fab | 0.1 | 8.9 | 0.1 |
| LC2t-Wild.1d | | | |
| aRSV-Fab | 2.2 | 2.4 | 9.2 |
| aTNFa-Fab | N.D. | N.D. | N.D. |
| aEGFR-Fab | N.D. | N.D. | N.D. |
| aHER2-Fab | 30.4 | 1.3 | 233.8 |
| aIgE-Fab | N.D. | N.D. | N.D. |
| aRANKL-Fab | N.D. | N.D. | N.D. |
| LC3t-Wild.1d | | | |
| aRSV-Fab | 1.8 | 2.1 | 8.7 |
| aTNFa-Fab | N.D. | N.D. | N.D. |
| aEGFR-Fab | N.D. | N.D. | N.D. |
| aHER2-Fab | 2.2 | 1.2 | 18.7 |
| aIgE-Fab | N.D. | N.D. | N.D. |
| aRANKL-Fab | N.D. | N.D. | N.D. |
| LC4t-Wild.1d | | | |
| aRSV-Fab | 3.4 | 1.7 | 19.3 |
| aTNFa-Fab | 0.1 | 39.7 | 0.02 |
| aEGFR-Fab | 0.2 | 25.3 | 0.1 |
| aHER2-Fab | 25.2 | 0.6 | 405.8 |
| aIgE-Fab | 52.3 | 0.1 | 4184.0 |
| aRANKL-Fab | 0.03 | 18.2 | 0.02 |

As the result shown in Tables 3 and 4, B1 to B4 domains and C1 to C4 domains derived from *Peptostreptococcus magnus* exhibited high affinity for the specific Fab regions in some cases but did not exhibit an affinity for the other Fab regions or the affinity was very low. On the one hand, as the result shown in Table 2, B5 domain derived from *Peptostreptococcus magnus* according to one or more embodiments of the present invention generally exhibited high affinity for all of the tested Fab regions. Thus, it was demonstrated that B5 domain according to one or more embodiments of the present invention is useful for purifying a peptide containing a Fab region.

Example 3: Preparation of Connected 4 Domains of PpL312 B5 Domains (LB5t-Wild.4d)

The amino acid sequence of SEQ ID NO: 26 (LB5t-Wild.4d) was designed. The amino acid sequence corresponded to 4 amino acid sequences of B5 domains of SEQ ID NO: 16 connected each other through the amino acid sequence between VL-κ-binding domains contained PpL312 of SEQ ID NO: 1. A base sequence of SEQ ID NO: 27 encoding the peptide was designed by reverse translation from the amino acid sequence of LB5t-Wild.4d (SEQ ID NO: 26). The artificially-synthesized DNA of SEQ ID NO: 28 was synthesized by outsourcing to Eurofins Genomics K.K. The DNA corresponded to the DNA of SEQ ID NO: 27 with the addition of PstI recognition site at the 5'-terminal and XbaI recognition site at the 3'-terminal. The expression plasmid after the subcloning was digested by restriction enzymes PstI and XbaI (Takara Bio Inc.). The obtained DNA fragment was ligated to *Brevibacillus* Expression vector pNCMO2 (Takara Bio Inc.) digested by the same restriction enzymes to prepare an expression vector corresponding to the *Brevibacillus* Expression vector pNCMO2 into which the DNA encoding the amino acid sequence of LB5t-Wild.4d was inserted. The ligation reaction was performed using Ligation high (manufactured by TOYOBO CO., LTD.) in accordance with the protocol attached to the product, and *Escherichia coli* JM109 (Takara Bio Inc.) was used for preparing the plasmid. The DNA base sequence of each expression vector was confirmed using DNA sequencer 3130xl Genetic Analyzer (Applied Biosystems). A PCR sequencing method of each plasmid DNA was conducted using BigDye Terminator v.1.1 Cycle Sequencing Kit (Applied Biosystems) in accordance with the attached protocol, and the obtained sequencing product was purified using a plasmid purification kit ("BigDye XTerminator Purification Kit" manufactured by Applied Biosystems) in accordance with the attached protocol to be used for sequence analysis.

*Brevibacillus choshinensis* SP3 (Takara Bio Inc.) was transformed using the obtained plasmid, and the obtained transformant which could produce and secrete LB5t-Wild.4d was cultivated. Specifically, the transformant was cultivated with shaking in 30 mL of culture medium A (polypeptone 3.0%, yeast extract 0.5%, glucose 3%, magnesium sulfate 0.01%, ferric sulfate 0.001%, manganese chloride 0.001%, zinc chloride 0.0001%) containing 60 μg/mL of neomycin at 30° C. for 3 days. After the cultivation, the culture solution was centrifuged at 15,000 rpm and at 25° C. for 5 minutes to separate the bacterial body.

From the obtained culture supernatant, LB5t-Wild.4d was purified by cation exchange chromatography using Uno-Sphere S (Bio-Rad). UnoSphere S was packed into Tricorn 10/200 (GE Healthcare Bioscience). Specifically, sodium acetate was added to the culture supernatant so that the final concentration became 50 mM, and the pH was adjusted to 4.0 using acetic acid. UnoSphere S column was equilibrated using a cation exchange buffer A (50 mM CH$_3$COOH—CH$_3$COONa, pH4.0). The culture supernatant was added to the column, and the column was washed using the cation exchange buffer A. Then, the cation exchange buffer A and a cation exchange buffer B (50 mM CH$_3$COOH—CH$_3$COONa, 1 M NaCl, pH4.0) were flown with concentration gradient of a salt, and LB5t-Wild.4d was collected during the elution. Next, LB5t-Wild.4d was purified by anion exchange chromatography using Nuvia Q column (Bio-Rad). Nuvia Q was packed into Tricorn 10/200 (GE Healthcare Bioscience). Specifically, the collected LB5t-Wild.4d solution was subjected to dialysis using an anion exchange buffer A (50 mM Tris-HCl, pH8.0). Nuvia Q column was equilibrated using the anion exchange buffer A. The collected LB5t-Wild.4d solution was added to the equilibrated Nuvia Q column, and the column was washed using the anion exchange buffer A. Then, the anion exchange buffer A and an anion exchange buffer B (50 mM Tris-HCl, 1.0 M NaCl, pH8.0) were flown with concentration gradient of a salt, and LB5t-Wild.4d was collected during the elution. The collected LB5t-Wild.4d was subjected to dialysis again using ultrapure water, and an aqueous solution containing LB5t-Wild.4d only was obtained as the final purified sample.

The protein purification by chromatography using the above-described columns was conducted using AKTAavant 25 system (GE Healthcare Bioscience).

Example 4: Preparation of Carrier on which Connected 4 Domains of PpL312 B5 Domains were Immobilized The LB5t-Wild.4d prepared in Example 3 was immobilized on a commercially available agarose base material. For the immobilization, the binding between the reactive amino acid residue of LB5t-Wild.4d and maleimide was used.

Specifically, 1.5 mL-gel of commercially available NHS-activated base material ("NHS Activated Sepharose 4 Fast Flow" manufactured by GE Healthcare Bioscience) was placed on a glass filter, and isopropanol as a preservative liquid was removed by suction. The base material was washed using 5 mL of iced 1 mM hydrochloric acid. Then, the base material was washed using 5 mL of a coupling buffer (20 mM $NaH_2PO_4$—$Na_2HPO_4$, 150 mM sodium chloride, pH7.2). The base material was recovered by dispersing the base material in the coupling buffer, and the dispersion was added into a centrifuge tube. A 10 mM solution of N-[ε-Maleimidocaproic acid]hydrazide·TFA (EMCH, Thermo Fisher Scientific K.K.) in the coupling buffer was added into the centrifuge tube containing the base material for the reaction at 25° C. for 1 hour. Then, the base material was placed on a glass filter for washing with 10 mL of a washing buffer A (0.5 M ethanolamine, 0.5 M sodium chloride, pH7.2), 10 mL of the coupling buffer and 10 mL of washing buffer A in the order. The raw material was stood still at 25° C. for 15 minutes. The raw material was further washed with 10 mL of the coupling buffer. By the procedure so far, maleimide was bound to the base material.

Next, LB5t-Wild.4d was immobilized on the base material to which maleimide was bound. Before the immobilization, LB5t-Wild.4d was reduced under the condition of 100 mM DTT, and was subjected to a pretreatment. In the pretreatment, the used DTT was removed by using a desalination column ("HiTrap Desalting" GE Healthcare Bioscience) and the buffer was changed to the coupling buffer. The base material on which maleimide was bound was added into a centrifuge tube, and a LB5t-Wild.4d solution further added thereto for the reaction at 25° C. for 2 hours to obtain a carrier. Then, the carrier was placed on a glass filter and washed with 7 mL of the coupling buffer to recover unreacted LB5t-Wild.4d. Next, the carrier was washed with 10 mL of a washing buffer B (50 mM L-cysteine, 100 mM $NaH_2PO_4$—$Na_2HPO_4$, 0.5 M sodium chloride, pH7.2), 10 mL of the coupling buffer and 10 mL of the washing buffer B in the order. The carrier was stood still at 25° C. for 15 minutes. The carrier was further washed with 10 mL of the coupling buffer, 10 mL of ultrapure water and 10 mL of 20% ethanol. Then, the carrier was dispersed in 20% ethanol and recovered to obtain LB5t-Wild.4d-immobilized carrier.

The absorbance of the recovered unreacted LB5t-Wild.4d at 280 nm was measured using a spectrometer. An amount of unreacted LB5t-T36H.4d was calculated from the measured absorbance and the absorption coefficient calculated from the amino acid sequence. An amount of the immobilized LB5t-Wild.4d was calculated from the difference of the amount of the used LB5t-Wild.4d and the calculated amount of the unreacted LB5t-Wild.4d, and the ligand density was further calculated from the volume of the carrier. The ligand densities of the prepared prototype carrier 1 and a commercially available Protein L carrier ("HiTrap Protein L" manufactured by GE Healthcare Bioscience) used as Comparative example 3 are shown in Table 5.

TABLE 5

| Carrier | Ligand density (mg/mL/gel) |
|---|---|
| Example 4 | 10 |
| Comparative example 3 | 10 |

Example 5: Confirmation of Adsorption of Polyclonal Fab on LB5t-Wild.4d-Immobilized Carrier The adsorption of human polyclonal Fab was evaluated in order to confirm the binding property of the LB5t-Wild.4d-immobilized carrier prepared in Example 4. As a human polyclonal Fab, a polyclonal Fab derived from human polyclonal antibody ("γ-GLOBULIN" manufactured by Nihon Pharmaceutical Co., Ltd.) was prepared. The human polyclonal Fab was prepared in accordance with Example 2(1), but IgG was recovered as an adsorbed component by affinity chromatography using KANEKA KanCapA™ column (KANEKA Corporation) before the treatment by papain and the recovered IgG was subjected to the treatment by papain, since the human polyclonal antibody contained a component which was not adsorbed on Protein A carrier.

Hereinafter, a method for confirming the binding property of the LB5t-Wild.4d-immobilized carrier is specifically described. Tricorn 5/50 column (GE Healthcare Bioscience) into which 1 mL-gel of the carrier was packed was connected to chromatosystem AKTAavant 25, and the column was equilibrated by flowing 3 CV of an equilibrating buffer (20 mM $NaH_2PO_4$—$Na_2HPO_4$, 150 mM sodium chloride, pH7.4) through the column in a flow rate of 0.25 mL/min. Next, 35 mL of 1 mg/mL human polyclonal Fab solution was flown through the column in a flow rate of 0.25 mL/min. Then, the human polyclonal Fab was eluted by flowing 10 CV of the equilibrating buffer and subsequently 10 CV of an eluting buffer (50 mM citric acid, pH3.0) through the column in a flow rate of 0.25 mL/min. Further, 3 CV of the equilibrating buffer was flown at a flow rate of 0.25 mL/min, and then 5 CV of a strong washing buffer (50 mM citric acid, pH2.5) was flown, and finally 5 CV of the equilibrating buffer was flown. A similar experiment was conducted using commercially available Protein L carrier ("HiTrap Protein L" manufactured by GE Healthcare Bioscience) as Comparative Example 3. The obtained chromatograph chart is shown as FIG. 3, and the enlarged part of the chromatography chart when human polyclonal Fab was added is shown as FIG. 4.

Figure 3:
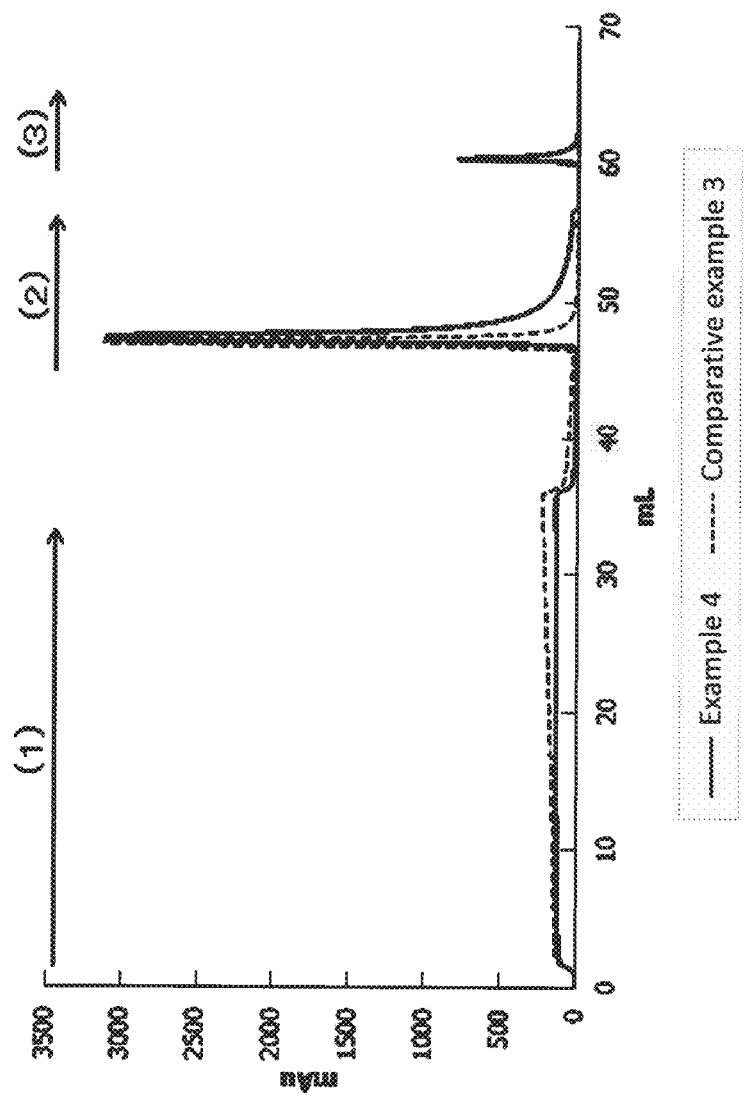
FIG. 3 is a chromatography chart of the case that polyclonal Fab was contacted with LB5t-Wild.4d-immobilized carrier or a commercially available Protein L carrier and then eluted by using an elution buffer and a strong washing solution.
Figure 4:
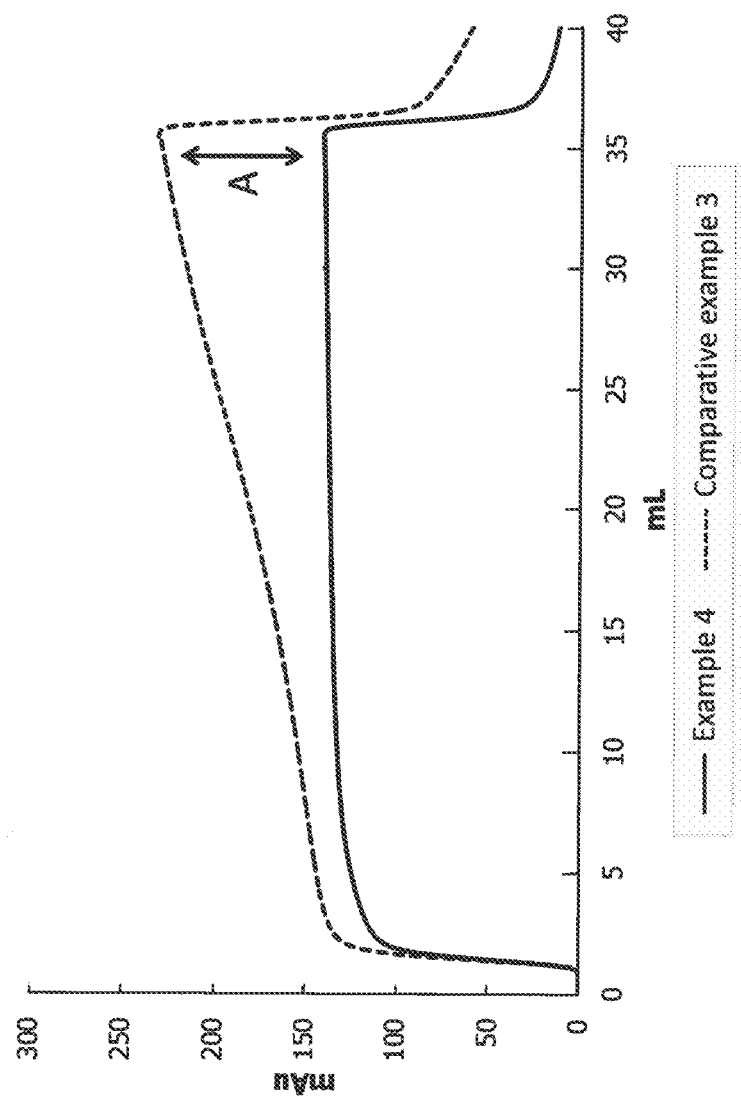
FIG. 4 is an enlarged part of the chromatography chart of FIG. 3 when polyclonal Fab was added.

The area of the peak of the elution fraction (2) in FIG. 3 in the case of using Example 4 is apparently larger than that of the case of using Comparative example 3. In addition, as the "difference A" in FIG. 4 corresponding an enlarged part of the step (1) for adding human polyclonal Fab, the leakage amount was continuously increased when human polyclonal Fab was added in the case of the carrier of Comparative example 3; on the one hand, the leakage amount was constant in the case of the carrier of Example 4. It was found that the added human polyclonal Fab was leaked, since there was a Fab which had λ chain variable region in human polyclonal Fab and the Fab having λ chain variable region was not adsorbed on the carriers of Comparative example 3 and Example 4. The "difference A" indicated that there was a Fab having a κ chain variable region, which was adsorbed on the carrier of Example 4 but was not adsorbed on the carrier of Comparative example 3. Thus, although the amounts of human polyclonal Fab which was added to each carrier were the same, the elution peak in the case of Example 4 was larger than that in the case of Comparative example 3, in other words, the amount of the adsorbed Fab in the case of Example 4 was larger than that in the case of Comparative example 3.

The above-described result indicated that the kind of an antibody fragment to be purified can be enlarged by using the affinity separation matrix on which the antibody κ chain variable region-binding peptide according to one or more embodiments of the present invention is immobilized as a ligand.

Example 6: Evaluation of Binding Capacity of LB5t-Wild.4d-Immobilized Carrier to Monoclonal Fab With respect to the LB5t-Wild.4d-immobilized carrier prepared in Example 4, a binding capacity to monoclonal Fab was evaluated. As the monoclonal Fab, a solution obtained by dissolving the aTNFa-Fab prepared in Example 2(1) in an equilibrating buffer (20 mM $NaH_2PO_4$—$Na_2HPO_4$, 150 mM sodium chloride, pH 7.4) in a concentration of 1 mg/mL was used.

Tricorn 5/50 column (manufactured by GE Healthcare Bioscience) packed with 1 mL-gel of the carrier was connected to chromatosystem AKTAavant 25, and 3 CV of an equilibrating buffer (20 mM $NaH_2PO_4$—$Na_2HPO_4$, 150 mM sodium chloride, pH 7.4) was flown at a flow rate of 0.25 mL/min for equilibration. Next, the aTNFa-Fab solution was flown at a flow rate of 0.25 mL/min until the monitoring absorbency exceeded 55% of 100% $Abs_{280}$. Then, 10 CV of the equilibrating buffer was flown at a flow rate of 0.25 mL/min, and subsequently 3 CV of an elution buffer (50 mM citric acid, pH 2.5) was flown to elute the aTNFa-Fab. The total amount of the aTNFa-Fab flown until the monitoring absorbency exceeded 55% of 100% $Abs_{280}$ was defined as 55% DBC for the aTNFa-Fab. A similar experiment was conducted except that commercially available Protein L carrier ("HiTrap Protein L" manufactured by GE Healthcare Bioscience) was used. The measurement result is shown in Table 6.

TABLE 6

| Carrier | 55% DBC (mg/mL/gel) |
| --- | --- |
| Example 4 | 48.6 |
| Comparative example 3 | 4.8 |

As the result shown in Table 6, the value of 55% DBC to aTNFa-Fab in the case of the carrier of Example 4 was much larger than that in the case of the carrier of Comparative example 3. The result indicates that the carrier of Comparative example 3 can hardly adsorb the Fab having κ chain variable region but such a Fab can be adsorbed and purified by using the affinity separation matrix on which the antibody κ chain variable region-binding peptide according to one or more embodiments of the present invention is immobilized as a ligand.

Although embodiments of the disclosure have been described using specific terms, devices, and methods, such description is for illustrative purposes only. The words used are words of description rather than limitation. It is to be understood that changes and variations may be made by those of ordinary skill in the art without departing from the spirit or the scope of the present disclosure, which is set forth in the following claims. In addition, it should be understood that aspects of the various embodiments may be interchanged in whole or in part. Therefore, the spirit and scope of the appended claims should not be limited to the description of the preferred versions contained therein.

What is claimed is:

1. An affinity separation matrix, comprising:
   a water-insoluble base material; and
   a ligand that is immobilized on the water-insoluble base material,
   wherein the ligand is an antibody κ chain variable region-binding peptide or a multimer thereof consisting essentially of at least one B5 domain of Protein L derived from *Peptostreptococcus magnus* 312 strain or a part thereof,
   wherein the antibody κ chain variable region-binding peptide consists of an amino acid sequence selected from the group consisting of:
      an amino acid sequence of SEQ ID NO: 7;
      an amino acid sequence of SEQ ID NO: 7 with deletion, substitution and/or addition of 1-10 amino acid residues, having a binding capability to an antibody κ chain variable region; and
      an amino acid sequence with a sequence identity of 85% or more to the amino acid sequence of SEQ ID NO: 7, having a binding capability to an antibody κ chain variable region, and
   wherein the 17th position is glutamic acid, the 19th position is isoleucine, the 20th position is tyrosine, the 22nd position is glutamic acid, the 25th position is threonine, the 26th position is valine, the 30th position is threonine, the 50th position is serine and the 53rd position is histidine.

2. An affinity separation matrix, comprising:
   a water-insoluble base material; and
   a ligand that is immobilized on the water-insoluble base material,
   wherein the ligand is an antibody κ chain variable region-binding peptide or a multimer thereof consisting essentially of at least one B5 domain of Protein L derived from *Peptostreptococcus magnus* 312 strain or a part thereof,
   wherein the antibody κ chain variable region-binding peptide consists of an amino acid sequence selected from the group consisting of:
      an amino acid sequence of SEQ ID NO: 16;
      an amino acid sequence of SEQ ID NO: 16 with deletion, substitution and/or addition of 1-10 amino acid residues, having a binding capability to an antibody κ chain variable region; and
      an amino acid sequence with a sequence identity of 85% or more to the amino acid sequence of SEQ ID NO: 16, having a binding capability to an antibody κ chain variable region, and
   wherein the 7th position is glutamic acid, the 9th position is isoleucine, the 10th position is tyrosine, the 12th position is glutamic acid, the 15th position is threonine, the 16th position is valine, the 20th position is threonine, the 40th position is serine and the 43rd position is histidine.

3. A method for producing a protein comprising an antibody κ chain variable region, the method comprising:
   contacting the affinity separation matrix according to claim 1 with a liquid sample comprising the protein comprising the antibody κ chain variable region; and
   separating the protein bound to the affinity separation matrix from the affinity separation matrix.

4. The affinity separation matrix according to claim 1, wherein the antibody κ chain variable region-binding peptide consists of the amino acid sequence of SEQ ID NO: 7.

5. The affinity separation matrix according to claim 2, wherein the antibody κ chain variable region-binding peptide consists of the amino acid sequence of SEQ ID NO: 16.

* * * * *

SEQUENCE LISTING

```
<160> NUMBER OF SEQ ID NOS: 28

<210> SEQ ID NO 1
<211> LENGTH: 719
<212> TYPE: PRT
<213> ORGANISM: Peptostreptococcus magnus

<400> SEQUENCE: 1

Met Ala Ala Leu Ala Gly Ala Ile Val Val Thr Gly Gly Val Gly Ser
1               5                   10                  15

Tyr Ala Ala Asp Glu Pro Ile Asp Leu Glu Lys Leu Glu Glu Lys Arg
            20                  25                  30

Asp Lys Glu Asn Val Gly Asn Leu Pro Lys Phe Asp Asn Glu Val Lys
        35                  40                  45

Asp Gly Ser Glu Asn Pro Met Ala Lys Tyr Pro Asp Phe Asp Asp Glu
    50                  55                  60

Ala Ser Thr Arg Phe Glu Thr Glu Asn Asn Glu Phe Glu Glu Lys Lys
65                  70                  75                  80

Val Val Ser Asp Asn Phe Phe Asp Gln Ser Glu His Pro Phe Val Glu
                85                  90                  95

Asn Lys Glu Glu Thr Pro Glu Thr Pro Glu Thr Asp Ser Glu Glu Glu
            100                 105                 110

Val Thr Ile Lys Ala Asn Leu Ile Phe Ala Asn Gly Ser Thr Gln Thr
```

-continued

```
            115                 120                 125
Ala Glu Phe Lys Gly Thr Phe Glu Lys Ala Thr Ser Glu Ala Tyr Ala
        130                 135                 140

Tyr Ala Asp Thr Leu Lys Lys Asp Asn Gly Glu Tyr Thr Val Asp Val
145                 150                 155                 160

Ala Asp Lys Gly Tyr Thr Leu Asn Ile Lys Phe Ala Gly Lys Glu Lys
                165                 170                 175

Thr Pro Glu Glu Pro Lys Glu Val Thr Ile Lys Ala Asn Leu Ile
            180                 185                 190

Tyr Ala Asp Gly Lys Thr Gln Thr Ala Glu Phe Lys Gly Thr Phe Glu
        195                 200                 205

Glu Ala Thr Ala Glu Ala Tyr Arg Tyr Ala Asp Ala Leu Lys Lys Asp
        210                 215                 220

Asn Gly Glu Tyr Thr Val Asp Val Ala Asp Lys Gly Tyr Thr Leu Asn
225                 230                 235                 240

Ile Lys Phe Ala Gly Lys Glu Lys Thr Pro Glu Glu Pro Lys Glu Glu
                245                 250                 255

Val Thr Ile Lys Ala Asn Leu Ile Tyr Ala Asp Gly Lys Thr Gln Thr
            260                 265                 270

Ala Glu Phe Lys Gly Thr Phe Glu Glu Ala Thr Ala Glu Ala Tyr Arg
        275                 280                 285

Tyr Ala Asp Leu Leu Ala Lys Glu Asn Gly Lys Tyr Thr Val Asp Val
        290                 295                 300

Ala Asp Lys Gly Tyr Thr Leu Asn Ile Lys Phe Ala Gly Lys Glu Lys
305                 310                 315                 320

Thr Pro Glu Glu Pro Lys Glu Val Thr Ile Lys Ala Asn Leu Ile
                325                 330                 335

Tyr Ala Asp Gly Lys Thr Gln Thr Ala Glu Phe Lys Gly Thr Phe Ala
            340                 345                 350

Glu Ala Thr Ala Glu Ala Tyr Arg Tyr Ala Asp Leu Leu Ala Lys Glu
        355                 360                 365

Asn Gly Lys Tyr Thr Ala Asp Leu Glu Asp Gly Gly Tyr Thr Ile Asn
        370                 375                 380

Ile Arg Phe Ala Gly Lys Lys Val Asp Glu Lys Pro Glu Glu Lys Glu
385                 390                 395                 400

Gln Val Thr Ile Lys Glu Asn Ile Tyr Phe Glu Asp Gly Thr Val Gln
                405                 410                 415

Thr Ala Thr Phe Lys Gly Thr Phe Ala Glu Ala Thr Ala Glu Ala Tyr
            420                 425                 430

Arg Tyr Ala Asp Leu Leu Ser Lys Glu His Gly Lys Tyr Thr Ala Asp
        435                 440                 445

Leu Glu Asp Gly Gly Tyr Thr Ile Asn Ile Arg Phe Ala Gly Lys Glu
        450                 455                 460

Glu Pro Glu Glu Thr Pro Glu Lys Pro Glu Val Gln Asp Gly Tyr Ala
465                 470                 475                 480

Ser Tyr Glu Glu Ala Glu Ala Ala Lys Glu Ala Leu Lys Asn Asp
                485                 490                 495

Asp Val Asn Lys Ser Tyr Thr Ile Arg Gln Gly Ala Asp Gly Arg Tyr
            500                 505                 510

Tyr Tyr Val Leu Ser Pro Val Glu Ala Glu Glu Glu Lys Pro Glu Ala
        515                 520                 525

Gln Asn Gly Tyr Ala Thr Tyr Glu Glu Ala Glu Ala Ala Lys Lys
        530                 535                 540
```

```
Ala Leu Glu Asn Asp Pro Ile Asn Lys Ser Tyr Ser Ile Arg Gln Gly
545                 550                 555                 560

Ala Asp Gly Arg Tyr Tyr Val Leu Ser Pro Val Glu Ala Glu Thr
            565                 570                 575

Pro Glu Lys Pro Val Glu Pro Ser Glu Pro Ser Thr Pro Asp Val Pro
            580                 585                 590

Ser Asn Pro Ser Asn Pro Ser Thr Pro Asp Val Pro Ser Thr Pro Asp
            595                 600                 605

Val Pro Ser Asn Pro Ser Thr Pro Glu Val Pro Ser Asn Pro Ser Thr
        610                 615                 620

Pro Gly Asn Glu Glu Lys Pro Gly Asn Glu Gln Lys Pro Gly Asn Glu
625                 630                 635                 640

Gln Lys Pro Gly Asn Glu Gln Lys Pro Gly Asn Glu Gln Lys Pro Gly
                645                 650                 655

Asn Glu Gln Lys Pro Asp Gln Pro Ser Lys Pro Glu Lys Glu Glu Asn
            660                 665                 670

Gly Lys Gly Gly Val Asp Ser Pro Lys Lys Glu Lys Ala Ala Leu
            675                 680                 685

Pro Lys Ala Gly Ser Glu Ala Glu Ile Leu Thr Leu Ala Ala Ala Ser
690                 695                 700

Leu Ser Ser Val Ala Gly Ala Phe Ile Ser Leu Lys Lys Arg Lys
705                 710                 715

<210> SEQ ID NO 2
<211> LENGTH: 992
<212> TYPE: PRT
<213> ORGANISM: Peptostreptococcus magnus

<400> SEQUENCE: 2

Met Lys Ile Asn Lys Lys Leu Leu Met Ala Ala Leu Ala Gly Ala Ile
1               5                   10                  15

Val Val Gly Gly Gly Ala Asn Ala Tyr Ala Ala Glu Glu Asp Asn Thr
            20                  25                  30

Asp Asn Asn Leu Ser Met Asp Glu Ile Ser Asp Ala Tyr Phe Asp Tyr
            35                  40                  45

His Gly Asp Val Ser Asp Ser Val Asp Pro Val Glu Glu Ile Asp
    50                  55                  60

Glu Ala Leu Ala Lys Ala Leu Ala Glu Ala Lys Glu Thr Ala Lys Lys
65                  70                  75                  80

His Ile Asp Ser Leu Asn His Leu Ser Glu Thr Ala Lys Lys Leu Ala
                85                  90                  95

Lys Asn Asp Ile Asp Ser Ala Thr Thr Ile Asn Ala Ile Asn Asp Ile
            100                 105                 110

Val Ala Arg Ala Asp Val Met Glu Arg Lys Thr Ala Glu Lys Glu Glu
        115                 120                 125

Ala Glu Lys Leu Ala Ala Lys Glu Thr Ala Lys Lys His Ile Asp
    130                 135                 140

Glu Leu Lys His Leu Ala Asp Lys Thr Lys Glu Leu Ala Lys Arg Asp
145                 150                 155                 160

Ile Asp Ser Ala Thr Thr Ile Asn Ala Ile Asn Asp Ile Val Ala Arg
                165                 170                 175

Ala Asp Val Met Glu Arg Lys Thr Ala Glu Lys Glu Ala Glu Lys
            180                 185                 190

Leu Ala Ala Ala Lys Glu Thr Ala Lys Lys His Ile Asp Glu Leu Lys
```

```
                    195                 200                 205
His Leu Ala Asp Lys Thr Lys Glu Leu Ala Lys Arg Asp Ile Asp Ser
210                 215                 220

Ala Thr Thr Ile Asp Ala Ile Asn Asp Ile Val Ala Arg Ala Asp Val
225                 230                 235                 240

Met Glu Arg Lys Leu Ser Glu Lys Glu Thr Pro Glu Pro Glu Glu Glu
                    245                 250                 255

Val Thr Ile Lys Ala Asn Leu Ile Phe Ala Asp Gly Ser Thr Gln Asn
                    260                 265                 270

Ala Glu Phe Lys Gly Thr Phe Ala Lys Ala Val Ser Asp Ala Tyr Ala
                275                 280                 285

Tyr Ala Asp Ala Leu Lys Lys Asp Asn Gly Glu Tyr Thr Val Asp Val
                290                 295                 300

Ala Asp Lys Gly Leu Thr Leu Asn Ile Lys Phe Ala Gly Lys Lys Glu
305                 310                 315                 320

Lys Pro Glu Glu Pro Lys Glu Glu Val Thr Ile Lys Val Asn Leu Ile
                    325                 330                 335

Phe Ala Asp Gly Lys Thr Gln Thr Ala Glu Phe Lys Gly Thr Phe Glu
                    340                 345                 350

Glu Ala Thr Ala Lys Ala Tyr Ala Tyr Ala Asp Leu Leu Ala Lys Glu
                355                 360                 365

Asn Gly Glu Tyr Thr Ala Asp Leu Glu Asp Gly Gly Asn Thr Ile Asn
370                 375                 380

Ile Lys Phe Ala Gly Lys Glu Thr Pro Glu Thr Pro Glu Glu Pro Lys
385                 390                 395                 400

Glu Glu Val Thr Ile Lys Val Asn Leu Ile Phe Ala Asp Gly Lys Ile
                    405                 410                 415

Gln Thr Ala Glu Phe Lys Gly Thr Phe Glu Glu Ala Thr Ala Lys Ala
                    420                 425                 430

Tyr Ala Tyr Ala Asn Leu Leu Ala Lys Glu Asn Gly Glu Tyr Thr Ala
                435                 440                 445

Asp Leu Glu Asp Gly Gly Asn Thr Ile Asn Ile Lys Phe Ala Gly Lys
                450                 455                 460

Glu Thr Pro Glu Thr Pro Glu Glu Pro Lys Glu Glu Val Thr Ile Lys
465                 470                 475                 480

Val Asn Leu Ile Phe Ala Asp Gly Lys Thr Gln Thr Ala Glu Phe Lys
                    485                 490                 495

Gly Thr Phe Glu Glu Ala Thr Ala Glu Ala Tyr Arg Tyr Ala Asp Leu
                    500                 505                 510

Leu Ala Lys Val Asn Gly Glu Tyr Thr Ala Asp Leu Glu Asp Gly Gly
                515                 520                 525

Tyr Thr Ile Asn Ile Lys Phe Ala Gly Lys Glu Gln Pro Gly Glu Asn
                530                 535                 540

Pro Gly Ile Thr Ile Asp Glu Trp Leu Leu Lys Asn Ala Lys Glu Glu
545                 550                 555                 560

Ala Ile Lys Glu Leu Lys Glu Ala Gly Ile Thr Ser Asp Leu Tyr Phe
                565                 570                 575

Ser Leu Ile Asn Lys Ala Lys Thr Val Glu Gly Val Glu Ala Leu Lys
                580                 585                 590

Asn Glu Ile Leu Lys Ala His Ala Gly Glu Glu Thr Pro Glu Leu Lys
                595                 600                 605

Asp Gly Tyr Ala Thr Tyr Glu Glu Ala Glu Ala Ala Lys Glu Ala
                610                 615                 620
```

Leu Lys Asn Asp Asp Val Asn Ala Tyr Glu Ile Val Gln Gly Ala
625                 630                 635                 640

Asp Gly Arg Tyr Tyr Tyr Val Leu Lys Ile Glu Val Ala Asp Glu Glu
            645                 650                 655

Glu Pro Gly Glu Asp Thr Pro Glu Val Gln Glu Gly Tyr Ala Thr Tyr
                660                 665                 670

Glu Glu Ala Glu Ala Ala Lys Glu Ala Leu Lys Glu Asp Lys Val
        675                 680                 685

Asn Asn Ala Tyr Glu Val Val Gln Gly Ala Asp Gly Arg Tyr Tyr Tyr
        690                 695                 700

Val Leu Lys Ile Glu Asp Lys Glu Asp Glu Gln Pro Gly Glu Glu Pro
705                 710                 715                 720

Gly Glu Asn Pro Gly Ile Thr Ile Asp Glu Trp Leu Leu Lys Asn Ala
                725                 730                 735

Lys Glu Asp Ala Ile Lys Glu Leu Lys Glu Ala Gly Ile Ser Ser Asp
                740                 745                 750

Ile Tyr Phe Asp Ala Ile Asn Lys Ala Lys Thr Val Glu Gly Val Glu
            755                 760                 765

Ala Leu Lys Asn Glu Ile Leu Lys Ala His Ala Glu Lys Pro Gly Glu
770                 775                 780

Asn Pro Gly Ile Thr Ile Asp Glu Trp Leu Leu Lys Asn Ala Lys Glu
785                 790                 795                 800

Ala Ala Ile Lys Glu Leu Lys Glu Ala Gly Ile Thr Ala Glu Tyr Leu
            805                 810                 815

Phe Asn Leu Ile Asn Lys Ala Lys Thr Val Glu Gly Val Glu Ser Leu
            820                 825                 830

Lys Asn Glu Ile Leu Lys Ala His Ala Glu Lys Pro Gly Glu Asn Pro
            835                 840                 845

Gly Ile Thr Ile Asp Glu Trp Leu Leu Lys Asn Ala Lys Glu Asp Ala
850                 855                 860

Ile Lys Glu Leu Lys Glu Ala Gly Ile Thr Ser Asp Ile Tyr Phe Asp
865                 870                 875                 880

Ala Ile Asn Lys Ala Lys Thr Ile Glu Gly Val Glu Ala Leu Lys Asn
            885                 890                 895

Glu Ile Leu Lys Ala His Lys Lys Asp Glu Glu Pro Gly Lys Lys Pro
            900                 905                 910

Gly Asp Lys Lys Pro Glu Asp Lys Lys Pro Gly Glu Asp Lys Lys
        915                 920                 925

Pro Glu Asp Lys Lys Pro Gly Glu Asp Lys Lys Pro Glu Asp Lys Lys
930                 935                 940

Pro Gly Lys Thr Asp Lys Asp Ser Pro Asn Lys Lys Lys Ala Lys
945                 950                 955                 960

Leu Pro Lys Ala Gly Ser Glu Ala Glu Ile Leu Thr Leu Ala Ala Ala
            965                 970                 975

Ala Leu Ser Thr Ala Ala Gly Ala Tyr Val Ser Leu Lys Lys Arg Lys
        980                 985                 990

<210> SEQ ID NO 3
<211> LENGTH: 76
<212> TYPE: PRT
<213> ORGANISM: Peptostreptococcus magnus

<400> SEQUENCE: 3

Lys Glu Glu Thr Pro Glu Thr Pro Glu Thr Asp Ser Glu Glu Glu Val

```
                1               5                  10                 15
Thr Ile Lys Ala Asn Leu Ile Phe Ala Asn Gly Ser Thr Gln Thr Ala
                               20                 25                 30

Glu Phe Lys Gly Thr Phe Glu Lys Ala Thr Ser Glu Ala Tyr Ala Tyr
                35                 40                 45

Ala Asp Thr Leu Lys Lys Asp Asn Gly Glu Tyr Thr Val Asp Val Ala
50                                 55                 60

Asp Lys Gly Tyr Thr Leu Asn Ile Lys Phe Ala Gly
65                  70                 75

<210> SEQ ID NO 4
<211> LENGTH: 72
<212> TYPE: PRT
<213> ORGANISM: Peptostreptococcus magnus

<400> SEQUENCE: 4

Lys Glu Lys Thr Pro Glu Glu Pro Lys Glu Glu Val Thr Ile Lys Ala
1               5                  10                 15

Asn Leu Ile Tyr Ala Asp Gly Lys Thr Gln Thr Ala Glu Phe Lys Gly
                20                 25                 30

Thr Phe Glu Glu Ala Thr Ala Glu Ala Tyr Arg Tyr Ala Asp Ala Leu
                35                 40                 45

Lys Lys Asp Asn Gly Glu Tyr Thr Val Asp Val Ala Asp Lys Gly Tyr
50                                 55                 60

Thr Leu Asn Ile Lys Phe Ala Gly
65                  70

<210> SEQ ID NO 5
<211> LENGTH: 72
<212> TYPE: PRT
<213> ORGANISM: Peptostreptococcus magnus

<400> SEQUENCE: 5

Lys Glu Lys Thr Pro Glu Glu Pro Lys Glu Glu Val Thr Ile Lys Ala
1               5                  10                 15

Asn Leu Ile Tyr Ala Asp Gly Lys Thr Gln Thr Ala Glu Phe Lys Gly
                20                 25                 30

Thr Phe Glu Glu Ala Thr Ala Glu Ala Tyr Arg Tyr Ala Asp Leu Leu
                35                 40                 45

Ala Lys Glu Asn Gly Lys Tyr Thr Val Asp Val Ala Asp Lys Gly Tyr
50                                 55                 60

Thr Leu Asn Ile Lys Phe Ala Gly
65                  70

<210> SEQ ID NO 6
<211> LENGTH: 72
<212> TYPE: PRT
<213> ORGANISM: Peptostreptococcus magnus

<400> SEQUENCE: 6

Lys Glu Lys Thr Pro Glu Glu Pro Lys Glu Glu Val Thr Ile Lys Ala
1               5                  10                 15

Asn Leu Ile Tyr Ala Asp Gly Lys Thr Gln Thr Ala Glu Phe Lys Gly
                20                 25                 30

Thr Phe Ala Glu Ala Thr Ala Glu Ala Tyr Arg Tyr Ala Asp Leu Leu
                35                 40                 45

Ala Lys Glu Asn Gly Lys Tyr Thr Ala Asp Leu Glu Asp Gly Gly Tyr
50                                 55                 60
```

```
Thr Ile Asn Ile Arg Phe Ala Gly
65                  70

<210> SEQ ID NO 7
<211> LENGTH: 73
<212> TYPE: PRT
<213> ORGANISM: Peptostreptococcus magnus

<400> SEQUENCE: 7

Lys Lys Val Asp Glu Lys Pro Glu Glu Lys Glu Gln Val Thr Ile Lys
1               5                   10                  15

Glu Asn Ile Tyr Phe Glu Asp Gly Thr Val Gln Thr Ala Thr Phe Lys
            20                  25                  30

Gly Thr Phe Ala Glu Ala Thr Ala Glu Ala Tyr Arg Tyr Ala Asp Leu
        35                  40                  45

Leu Ser Lys Glu His Gly Lys Tyr Thr Ala Asp Leu Glu Asp Gly Gly
    50                  55                  60

Tyr Thr Ile Asn Ile Arg Phe Ala Gly
65                  70

<210> SEQ ID NO 8
<211> LENGTH: 71
<212> TYPE: PRT
<213> ORGANISM: Peptostreptococcus magnus

<400> SEQUENCE: 8

Lys Glu Thr Pro Glu Pro Glu Glu Val Thr Ile Lys Ala Asn Leu
1               5                   10                  15

Ile Phe Ala Asp Gly Ser Thr Gln Asn Ala Glu Phe Lys Gly Thr Phe
            20                  25                  30

Ala Lys Ala Val Ser Asp Ala Tyr Ala Tyr Ala Asp Ala Leu Lys Lys
        35                  40                  45

Asp Asn Gly Glu Tyr Thr Val Asp Val Ala Asp Lys Gly Leu Thr Leu
    50                  55                  60

Asn Ile Lys Phe Ala Gly Lys
65                  70

<210> SEQ ID NO 9
<211> LENGTH: 71
<212> TYPE: PRT
<213> ORGANISM: Peptostreptococcus magnus

<400> SEQUENCE: 9

Lys Glu Lys Pro Glu Glu Pro Lys Glu Glu Val Thr Ile Lys Val Asn
1               5                   10                  15

Leu Ile Phe Ala Asp Gly Lys Thr Gln Thr Ala Glu Phe Lys Gly Thr
            20                  25                  30

Phe Glu Glu Ala Thr Ala Lys Ala Tyr Ala Tyr Ala Asp Leu Leu Ala
        35                  40                  45

Lys Glu Asn Gly Glu Tyr Thr Ala Asp Leu Glu Asp Gly Gly Asn Thr
    50                  55                  60

Ile Asn Ile Lys Phe Ala Gly
65                  70

<210> SEQ ID NO 10
<211> LENGTH: 74
<212> TYPE: PRT
<213> ORGANISM: Peptostreptococcus magnus
```

```
<400> SEQUENCE: 10

Lys Glu Thr Pro Glu Thr Pro Glu Pro Lys Glu Val Thr Ile
1               5                   10                  15

Lys Val Asn Leu Ile Phe Ala Asp Gly Lys Ile Gln Thr Ala Glu Phe
            20                  25                  30

Lys Gly Thr Phe Glu Glu Ala Thr Ala Lys Ala Tyr Ala Tyr Ala Asn
        35                  40                  45

Leu Leu Ala Lys Glu Asn Gly Glu Tyr Thr Ala Asp Leu Glu Asp Gly
    50                  55                  60

Gly Asn Thr Ile Asn Ile Lys Phe Ala Gly
65                  70

<210> SEQ ID NO 11
<211> LENGTH: 75
<212> TYPE: PRT
<213> ORGANISM: Peptostreptococcus magnus

<400> SEQUENCE: 11

Lys Glu Thr Pro Glu Thr Pro Glu Glu Pro Lys Glu Val Thr Ile
1               5                   10                  15

Lys Val Asn Leu Ile Phe Ala Asp Gly Lys Thr Gln Thr Ala Glu Phe
            20                  25                  30

Lys Gly Thr Phe Glu Glu Ala Thr Ala Glu Ala Tyr Arg Tyr Ala Asp
        35                  40                  45

Leu Leu Ala Lys Val Asn Gly Glu Tyr Thr Ala Asp Leu Glu Asp Gly
    50                  55                  60

Gly Tyr Thr Ile Asn Ile Lys Phe Ala Gly Lys
65                  70                  75

<210> SEQ ID NO 12
<211> LENGTH: 63
<212> TYPE: PRT
<213> ORGANISM: Peptostreptococcus magnus

<400> SEQUENCE: 12

Glu Glu Val Thr Ile Lys Ala Asn Leu Ile Phe Ala Asn Gly Ser Thr
1               5                   10                  15

Gln Thr Ala Glu Phe Lys Gly Thr Phe Glu Lys Ala Thr Ser Glu Ala
            20                  25                  30

Tyr Ala Tyr Ala Asp Thr Leu Lys Lys Asp Asn Gly Glu Tyr Thr Val
        35                  40                  45

Asp Val Ala Asp Lys Gly Tyr Thr Leu Asn Ile Lys Phe Ala Gly
    50                  55                  60

<210> SEQ ID NO 13
<211> LENGTH: 63
<212> TYPE: PRT
<213> ORGANISM: Peptostreptococcus magnus

<400> SEQUENCE: 13

Glu Glu Val Thr Ile Lys Ala Asn Leu Ile Tyr Ala Asp Gly Lys Thr
1               5                   10                  15

Gln Thr Ala Glu Phe Lys Gly Thr Phe Glu Glu Ala Thr Ala Glu Ala
            20                  25                  30

Tyr Arg Tyr Ala Asp Ala Leu Lys Lys Asp Asn Gly Glu Tyr Thr Val
        35                  40                  45

Asp Val Ala Asp Lys Gly Tyr Thr Leu Asn Ile Lys Phe Ala Gly
    50                  55                  60
```

<210> SEQ ID NO 14
<211> LENGTH: 63
<212> TYPE: PRT
<213> ORGANISM: Peptostreptococcus magnus

<400> SEQUENCE: 14

Glu Glu Val Thr Ile Lys Ala Asn Leu Ile Tyr Ala Asp Gly Lys Thr
1               5                   10                  15

Gln Thr Ala Glu Phe Lys Gly Thr Phe Glu Ala Thr Ala Glu Ala
            20                  25                  30

Tyr Arg Tyr Ala Asp Leu Leu Ala Lys Glu Asn Gly Lys Tyr Thr Val
        35                  40                  45

Asp Val Ala Asp Lys Gly Tyr Thr Leu Asn Ile Lys Phe Ala Gly
    50                  55                  60

<210> SEQ ID NO 15
<211> LENGTH: 63
<212> TYPE: PRT
<213> ORGANISM: Peptostreptococcus magnus

<400> SEQUENCE: 15

Glu Glu Val Thr Ile Lys Ala Asn Leu Ile Tyr Ala Asp Gly Lys Thr
1               5                   10                  15

Gln Thr Ala Glu Phe Lys Gly Thr Phe Ala Glu Ala Thr Ala Glu Ala
            20                  25                  30

Tyr Arg Tyr Ala Asp Leu Leu Ala Lys Glu Asn Gly Lys Tyr Thr Ala
        35                  40                  45

Asp Leu Glu Asp Gly Gly Tyr Thr Ile Asn Ile Arg Phe Ala Gly
    50                  55                  60

<210> SEQ ID NO 16
<211> LENGTH: 63
<212> TYPE: PRT
<213> ORGANISM: Peptostreptococcus magnus

<400> SEQUENCE: 16

Glu Gln Val Thr Ile Lys Glu Asn Ile Tyr Phe Glu Asp Gly Thr Val
1               5                   10                  15

Gln Thr Ala Thr Phe Lys Gly Thr Phe Ala Glu Ala Thr Ala Glu Ala
            20                  25                  30

Tyr Arg Tyr Ala Asp Leu Leu Ser Lys Glu His Gly Lys Tyr Thr Ala
        35                  40                  45

Asp Leu Glu Asp Gly Gly Tyr Thr Ile Asn Ile Arg Phe Ala Gly
    50                  55                  60

<210> SEQ ID NO 17
<211> LENGTH: 64
<212> TYPE: PRT
<213> ORGANISM: Peptostreptococcus magnus

<400> SEQUENCE: 17

Glu Glu Val Thr Ile Lys Ala Asn Leu Ile Phe Ala Asp Gly Ser Thr
1               5                   10                  15

Gln Asn Ala Glu Phe Lys Gly Thr Phe Ala Lys Ala Val Ser Asp Ala
            20                  25                  30

Tyr Ala Tyr Ala Asp Ala Leu Lys Lys Asp Asn Gly Glu Tyr Thr Val
        35                  40                  45

Asp Val Ala Asp Lys Gly Leu Thr Leu Asn Ile Lys Phe Ala Gly Lys

<210> SEQ ID NO 18
<211> LENGTH: 63
<212> TYPE: PRT
<213> ORGANISM: Peptostreptococcus magnus

<400> SEQUENCE: 18

Glu Glu Val Thr Ile Lys Val Asn Leu Ile Phe Ala Asp Gly Lys Thr
1               5                   10                  15
Gln Thr Ala Glu Phe Lys Gly Thr Phe Glu Glu Ala Thr Ala Lys Ala
            20                  25                  30
Tyr Ala Tyr Ala Asp Leu Leu Ala Lys Glu Asn Gly Lys Tyr Thr Ala
        35                  40                  45
Asp Leu Glu Asp Gly Gly Asn Thr Ile Asn Ile Lys Phe Ala Gly
    50                  55                  60

<210> SEQ ID NO 19
<211> LENGTH: 63
<212> TYPE: PRT
<213> ORGANISM: Peptostreptococcus magnus

<400> SEQUENCE: 19

Glu Glu Val Thr Ile Lys Val Asn Leu Ile Phe Ala Asp Gly Lys Ile
1               5                   10                  15
Gln Thr Ala Glu Phe Lys Gly Thr Phe Glu Glu Ala Thr Ala Lys Ala
            20                  25                  30
Tyr Ala Tyr Ala Asn Leu Leu Ala Lys Glu Asn Gly Glu Tyr Thr Ala
        35                  40                  45
Asp Leu Glu Asp Gly Gly Asn Thr Ile Asn Ile Lys Phe Ala Gly
    50                  55                  60

<210> SEQ ID NO 20
<211> LENGTH: 64
<212> TYPE: PRT
<213> ORGANISM: Peptostreptococcus magnus

<400> SEQUENCE: 20

Glu Glu Val Thr Ile Lys Val Asn Leu Ile Phe Ala Asp Gly Lys Thr
1               5                   10                  15
Gln Thr Ala Glu Phe Lys Gly Thr Phe Glu Glu Ala Thr Ala Glu Ala
            20                  25                  30
Tyr Arg Tyr Ala Asp Leu Leu Ala Lys Val Asn Gly Glu Tyr Thr Ala
        35                  40                  45
Asp Leu Glu Asp Gly Gly Tyr Thr Ile Asn Ile Lys Phe Ala Gly Lys
    50                  55                  60

<210> SEQ ID NO 21
<211> LENGTH: 195
<212> TYPE: DNA
<213> ORGANISM: Artificial Sequence
<220> FEATURE:
<223> OTHER INFORMATION: PpL cDNA

<400> SEQUENCE: 21
tccgaacagg ttaccattaa agagaacatc tactttgaag atggcacggt acagactgcc      60
acgttcaaag gtacgtttgc ggaagctact gcagaagctt accgctatgc ggacctgctc     120
tcgaaagagc atggcaaata cacagcggat cttgaagatg gaggttacac aatcaatatt     180
cgcttcgccg gctaa                                                      195

<210> SEQ ID NO 22
<211> LENGTH: 66
<212> TYPE: DNA
<213> ORGANISM: Artificial Sequence
<220> FEATURE:
<223> OTHER INFORMATION: oligo DNA

<400> SEQUENCE: 22

```
cgtggatccg aacaggttac cattaaagag aacatctact ttgaagatgg cacggtacag      60
actgcc                                                                 66
```

<210> SEQ ID NO 23
<211> LENGTH: 54
<212> TYPE: DNA
<213> ORGANISM: Artificial Sequence
<220> FEATURE:
<223> OTHER INFORMATION: oligo DNA

<400> SEQUENCE: 23

```
gcggtaagct tctgcagtag cttccgcaaa cgtacctttg aacgtggcag tctg            54
```

<210> SEQ ID NO 24
<211> LENGTH: 63
<212> TYPE: DNA
<213> ORGANISM: Artificial Sequence
<220> FEATURE:
<223> OTHER INFORMATION: oligo DNA

<400> SEQUENCE: 24

```
gcagaagctt accgctatgc ggacctgctc tcgaaagagc atggcaaata cacagcggat      60
ctt                                                                    63
```

<210> SEQ ID NO 25
<211> LENGTH: 60
<212> TYPE: DNA
<213> ORGANISM: Artificial Sequence
<220> FEATURE:
<223> OTHER INFORMATION: oligo DNA

<400> SEQUENCE: 25

```
gatgaattct tagccggcga agcgaatatt gattgtgtaa cctccatctt caagatccgc      60
```

<210> SEQ ID NO 26
<211> LENGTH: 302
<212> TYPE: PRT
<213> ORGANISM: Artificial Sequence
<220> FEATURE:
<223> OTHER INFORMATION: PpL mutant

<400> SEQUENCE: 26

```
Lys Glu Glu Thr Pro Glu Thr Pro Glu Thr Asp Ser Glu Glu Gln Val
1               5                   10                  15

Thr Ile Lys Glu Asn Ile Tyr Phe Glu Asp Gly Thr Val Gln Thr Ala
            20                  25                  30

Thr Phe Lys Gly Thr Phe Ala Glu Ala Thr Ala Glu Ala Tyr Arg Tyr
        35                  40                  45

Ala Asp Leu Leu Ser Lys Glu His Gly Lys Tyr Thr Ala Asp Leu Glu
    50                  55                  60

Asp Gly Gly Tyr Thr Ile Asn Ile Arg Phe Ala Gly Lys Glu Lys Thr
65                  70                  75                  80

Pro Glu Glu Pro Lys Glu Gln Val Thr Ile Lys Glu Asn Ile Tyr Phe
```

|  | 85 |  |  |  |  | 90 |  |  |  |  | 95 |  |
|---|---|---|---|---|---|---|---|---|---|---|---|---|

Glu Asp Gly Thr Val Gln Thr Ala Thr Phe Lys Gly Thr Phe Ala Glu
                100                          105                         110

Ala Thr Ala Glu Ala Tyr Arg Tyr Ala Asp Leu Leu Ser Lys Glu His
        115                        120                        125

Gly Lys Tyr Thr Ala Asp Leu Glu Asp Gly Gly Tyr Thr Ile Asn Ile
 130                         135                         140

Arg Phe Ala Gly Lys Glu Lys Thr Pro Glu Glu Pro Lys Glu Gln Val
145                    150                        155                        160

Thr Ile Lys Glu Asn Ile Tyr Phe Glu Asp Gly Thr Val Gln Thr Ala
                  165                        170                        175

Thr Phe Lys Gly Thr Phe Ala Glu Ala Thr Ala Glu Ala Tyr Arg Tyr
                180                        185                        190

Ala Asp Leu Leu Ser Lys Glu His Gly Lys Tyr Thr Ala Asp Leu Glu
                195                        200                        205

Asp Gly Gly Tyr Thr Ile Asn Ile Arg Phe Ala Gly Lys Glu Lys Thr
    210                        215                         220

Pro Glu Glu Pro Lys Glu Gln Val Thr Ile Lys Glu Asn Ile Tyr Phe
225                    230                        235                        240

Glu Asp Gly Thr Val Gln Thr Ala Thr Phe Lys Gly Thr Phe Ala Glu
                  245                        250                        255

Ala Thr Ala Glu Ala Tyr Arg Tyr Ala Asp Leu Leu Ser Lys Glu His
                    260                        265                        270

Gly Lys Tyr Thr Ala Asp Leu Glu Asp Gly Gly Tyr Thr Ile Asn Ile
        275                        280                         285

Arg Phe Ala Gly Lys Lys Val Asp Glu Lys Pro Glu Glu Cys
              290                        295                        300

```
<210> SEQ ID NO 27
<211> LENGTH: 906
<212> TYPE: DNA
<213> ORGANISM: Artificial Sequence
<220> FEATURE:
<223> OTHER INFORMATION: DNA code

<400> SEQUENCE: 27
aaagaagaaa ccccggaaac cccagaaacc gactctgaag aacaggtcac aatcaaggaa    60
aacatttatt ttgaagatgg taccgtgcaa accgcaactt ttaaaggcac attcgctgaa   120
gctacggcgg aggcgtatcg ttacgcggac ttactgtcga agaacatggt aaatatacc    180 gccgatctgg aagatggcgg ctataccatt aacattcgct cgcaggcaa agagaagacc    240 cctgaagaac cgaaggaaca ggtgaccatt aaagagaata tctatttcga agacggtact   300
gtacagaccg cgacgtttaa aggaaccttt gccgaagcca cggccgaggc ttatcgctac   360
gccgatcttc tgtccaaaga gcatggcaag tacacggcgg acctggagga tggggttac    420 actatcaaca ttcggtttgc gggtaaggaa aaacaccgg aagaacccaa agaacaagtc    480
actatcaaag agaacattta ctttgaggac ggcacggttc aaacggcaac cttcaaaggg   540
acgtttgcgg aagcgacagc agaagcctac cgctatgctg atctactgag caaagaacac   600
ggcaagtata ctgcggattt ggaagacgga ggttacacca tcaatatccg attcgcgggc   660
aaagaaaaaa ctccagaaga gccgaaagag caggttacca taaagaaaa tatttacttc   720 gaagatggca ccgtacagac ggcaacattc aagggtaccc ttgctgaggc aaccgccgaa   780
gcataccgtt atgccgacct cctgagtaaa gagcacggaa aatatacggc ggatttagag   840
```

-continued

```
gatggcggtt atacgatcaa tattcgtttt gccgggaaaa aagtggatga aaaaccggag    900
gaatgc                                                               906

<210> SEQ ID NO 28
<211> LENGTH: 923
<212> TYPE: DNA
<213> ORGANISM: Artificial Sequence
<220> FEATURE:
<223> OTHER INFORMATION: DNA code

<400> SEQUENCE: 28
ctgcaggaaa agaagaaacc ccggaaaccc cagaaaccga ctctgaagaa caggtcacaa     60
tcaaggaaaa catttatttt gaagatggta ccgtgcaaac cgcaactttt aaaggcacat    120
tcgctgaagc tacggcggag gcgtatcgtt acgcggactt actgtcgaaa gaacatggta    180
aatataccgc cgatctggaa gatggcggct ataccattaa cattcgcttc gcaggcaaag    240
agaagacccc tgaagaaccg aaggaacagg tgaccattaa agagaatatc tatttcgaag    300
acggtactgt acagaccgcg acgtttaaag gaacctttgc cgaagccacg gccgaggctt    360
atcgctacgc cgatcttctg tccaaagagc atggcaagta cacggcggac ctggaggatg    420
ggggttacac tatcaacatt cggtttgcgg gtaaggaaaa aacaccggaa gaacccaaag    480
aacaagtcac tatcaaagag aacatttact ttgaggacgg cacggttcaa acggcaacct    540
tcaaagggac gtttgcggaa gcgacagcag aagcctaccg ctatgctgat ctactgagca    600
aagaacacgg caagtatact gcggatttgg aagacggagg ttacaccatc aatatccgat    660
tcgcgggcaa agaaaaaact ccagaagagc cgaaagagca ggttaccata aaagaaaata    720
tttacttcga agatggcacc gtacagacgg caacattcaa gggtaccttt gctgaggcaa    780
ccgccgaagc ataccgttat gccgacctcc tgagtaaaga gcacggaaaa tatacggcgg    840
atttagagga tggcggttat acgatcaata ttcgttttgc cgggaaaaaa gtggatgaaa    900
aaccggagga atgctaatct aga                                            923
```